(12) United States Patent  
Chen et al.

(10) Patent No.: US 10,627,388 B2  
(45) Date of Patent: Apr. 21, 2020

(54) METHOD FOR DETECTING A DEFLECTION, SCANNING APPARATUS, AND USE OF A BLOCKING DEVICE FOR DETECTING A DEFLECTION

(71) Applicant: ABB Schweiz AG, Baden (CH)

(72) Inventors: Shih-Chin Chen, Dublin, OH (US); Chang Yuan Liu, Columbus, OH (US); Ake A. Hellstrom, Columbus, OH (US)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 16/341,505

(22) PCT Filed: Sep. 27, 2017

(86) PCT No.: PCT/EP2017/074445  
§ 371 (c)(1),  
(2) Date: Apr. 12, 2019

(87) PCT Pub. No.: WO2018/069042  
PCT Pub. Date: Apr. 19, 2018

(65) Prior Publication Data  
US 2019/0302090 A1 Oct. 3, 2019

(30) Foreign Application Priority Data  
Oct. 14, 2016 (EP) .................... 16194011

(51) Int. Cl.  
*G01N 21/00* (2006.01)  
*G01N 33/34* (2006.01)  
(Continued)

(52) U.S. Cl.  
CPC ....... *G01N 33/346* (2013.01); *G01N 21/3559* (2013.01); *G01N 21/59* (2013.01); *G01N 21/86* (2013.01); *G01N 2021/8609* (2013.01)

(58) Field of Classification Search  
CPC ...... G01N 21/89; G01N 21/86; G01N 21/896; G01N 21/3559; G01N 21/8983; G01N 33/346; G01N 33/367; G01N 2021/8663  
(Continued)

(56) References Cited

U.S. PATENT DOCUMENTS 3,813,173 A * 5/1974 Teter ................ G01N 21/95623  
356/239.7  
4,692,616 A * 9/1987 Hegland ................ G01D 18/00  
250/252.1  
(Continued)

FOREIGN PATENT DOCUMENTS

CN 1279398 A 1/2001  
CN 101379391 A 3/2009  
(Continued)

OTHER PUBLICATIONS

International Search Report & Written Opinion of the International Searching Authority Application No. PCT/EP2017/074445 Completed: Oct. 24, 2017; dated Nov. 6, 2017 12 Pages.  
(Continued)

*Primary Examiner* — Hoa Q Pham  
(74) *Attorney, Agent, or Firm* — Whitmyer IP Group LLC

(57) ABSTRACT

A method for detecting a deflection between a source module and a detection module in a scanning apparatus and configured as a sensor pair for scanning transmission measurement of sheet material being transported in a machine direction through a sensing gap formed between the source module and the detection module. The source module is arranged on a first side of the sensing gap and emits a sensing radiation or sensing energy radiation towards the sensing gap, and the detection module is arranged on a second side of the sensing gap opposite to the first side and detects the radiation from the source module and transmitted through the sensing gap. The method includes: attaching a  
(Continued)

removable blocking device to the detection module; and performing a partially-blocked scanning process during which the source module and the detection module are jointly moved in a cross direction of the scanning apparatus.

20 Claims, 19 Drawing Sheets

(51) Int. Cl.
*G01N 21/3559* (2014.01)
*G01N 21/59* (2006.01)
*G01N 21/86* (2006.01)

(58) Field of Classification Search
USPC .......... 356/429–431, 239.1, 238.1, 637–638, 356/237.1–237.5; 250/559.12, 559.42, 250/548
See application file for complete search history.

(56) References Cited

U.S. PATENT DOCUMENTS

| | | | | |
|---|---|---|---|---|
| 5,773,714 | A | 6/1998 | Shead | |
| 6,872,895 | B2* | 3/2005 | Cochran | G01F 17/00 |
| | | | | 177/1 |
| 6,960,769 | B2* | 11/2005 | Burk | G01N 21/86 |
| | | | | 250/228 |
| 7,528,400 | B2* | 5/2009 | Duck | D21F 7/06 |
| | | | | 250/559.23 |
| 8,148,690 | B2* | 4/2012 | Sturm | G01N 21/86 |
| | | | | 250/339.07 |
| 9,612,213 | B2* | 4/2017 | Meijer Drees | G01N 23/09 |
| 2004/0065829 | A1* | 4/2004 | Burk | G01N 21/86 |
| | | | | 250/339.07 |
| 2006/0243931 | A1* | 11/2006 | Haran | G01N 21/3554 |
| | | | | 250/574 |
| 2011/0068261 | A1* | 3/2011 | Sturm | G01N 21/86 |
| | | | | 250/252.1 |
| 2013/0100503 | A1 | 4/2013 | Beselt | |
| 2013/0289918 | A1 | 10/2013 | Haran et al. | |
| 2016/0123773 | A1 | 5/2016 | Beselt | |

FOREIGN PATENT DOCUMENTS

| | | |
|---|---|---|
| CN | 104067094 A | 9/2014 |
| CN | 104254759 A | 12/2014 |

OTHER PUBLICATIONS

European Search Report Application No. 16194011.9 Completed: Mar. 21, 2017; dated Mar. 31, 2017 5 Pages.
Chinese Office Action, Translation and Search Report Application 201780063322.2 Completed: Aug. 17, 2019; dated Aug. 27, 2019 7 Pages.
Office Action from Canada Application No. 3,040,563 completed Jan. 14, 2020 5 pages.

* cited by examiner

CD deflection profile monotonically sloping (associated to tension difference between top and bottom drive belts)

Oscillation with multiple harmonics (associated with wearing or defects of carriage wheels)

| Symptom | Pass | Value | Limit | Action |
|---|---|---|---|---|
| CD slope | ☐ | 0.4673 | 0.0500 | belt & phasing |
| CD offset | ☐ | 0.1121 | 0.1000 | Adjust phas... |
| MD offset | ☐ | 0.2065 | 0.0500 | Adjust top h... |
| Wheels | ☑ | 0.0051 | 0.0320 | N/A |
| CD F-R offset | ☑ | 0.0067 | 0.0500 | N/A |
| MD F-R offset | ☑ | 0.0283 | 0.0500 | N/A |
| Gap F-R offset | ☑ | 0.0047 | 0.0500 | N/A |

Action

Adjust belt & phasing

METHOD FOR DETECTING A DEFLECTION, SCANNING APPARATUS, AND USE OF A BLOCKING DEVICE FOR DETECTING A DEFLECTION

TECHNICAL FIELD

The present application relates to a method for detecting a deflection of a scanning apparatus, and an use of a blocking device for detecting a deflection, and specifically to method for detecting a deflection between a source module and a detection module in a scanning apparatus and configured as a sensor pair for scanning transmission measurement of sheet material being transported in a machine direction through a sensing gap formed between the source module and the detection module, a scanning apparatus being configured for scanning transmission measurement of sheet material being transported in a machine direction through a sensing gap of the scanning apparatus, and an use of a blocking device for detecting a deflection of a scanning apparatus configured for scanning transmission measurement of sheet material being transported in a machine direction through a sensing gap formed between a source module and a detection module of the scanning apparatus from a partially-blocked sensor signal obtained from a partially-blocked scanning process.

BACKGROUND

For most of sheet-making processes, an online quality measurement and control system (QCS) is an equipment useful to achieve intended sheet qualities and to optimize production throughput. In a QCS, one of the mechanical components of interest is a scanning apparatus 100 that allows multiple online sheet quality measuring sensors to be mounted thereon. Scanning apparatuses 100 are typically constructed as a rectangular structure where top and bottom beams 112, 114 are supported with two end columns 116, 118 as shown in FIG. 1. Sheet material 80 can travel through an open space between top and bottom beams 112, 114.

Online sheet quality measuring sensors typically include two modules, one module 130 including a source is mounted on a carriage 330 movable on one beam 114 and the other module 140 including a detector is mounted on another carriage 340 movable on the other beam 112. During production, the sheet material 80 or continuously produced sheet material 80 hence travels between two sensor modules 130, 140 which are carried by the top and bottom carriages 330, 340, respectively. Usually a constant source signal is transmitted from the source module 130 through the moving sheet material 80 and is detected by the detection module 140. A variation in the detected signal can be used to determine sheet quality variations. In this setup, the top and bottom carriages 330, 340 are synchronized and jointly traverse back and forth in a cross direction CD for scanning 50 between sheet edges 81, 82 while the sheet material is moving through a sensing gap 150 between the source module 130 and the detection module 140. A system 400 takes the detected signal from the detection module 140 and the carriage moving position to build scanning measurement 401 as a function of cross direction CD position. The scanning measurement 401 can also be referred to as profile.

In order to achieve high precision sheet quality measurements, it can be ensured that the source module 130 and the detection module 140 are aligned precisely while they are traversing back and forth 50 in a cross direction CD and, e.g., perform a forward scan 51 and/or a reverse scan 52. The alignment between the source module 130 and the detection module 140 can be obtained with a number of ways. For instance, mechanical dial indicators or magnetic alignment sensors can be mounted on the top and bottom carriages 330, 340 to detect misalignments, also known as deflections D, between the top and bottom carriages 330, 340 and/or between the source module 130 and the detection module 140. The detected deflection D can be used for diagnostics of conditions of mechanical components or operations of the scanning apparatus 100, e.g., to control carriage movement, and/or to compensate the impacts of deflection on sensor measurements.

However, in practice, mechanical dial indicators are bulky, fragile and difficult to mount, and adding magnetic alignment sensors to an existing scanning apparatus 100 may not be a trivial upgrade. Adding new magnetic alignment sensors like Hall-effect sensors or their equivalent usually involves various degrees of mechanical alternation to a scanning apparatus 100 and/or significant software changes that may or may not be even feasible for older QCS systems.

In reality, there are tens of thousands of scanning apparatuses that have been installed and continue being in use around the world in the past several decades. Even though some older scanning apparatuses may have been shut-down, upgraded or replaced, there are still large number of different generations of scanning apparatuses currently in operation. From a practical point of view, all scanning apparatuses in operation will need regular check-up of their mechanical conditions in order to provide solid foundation for online sheet quality sensors to get high precision measurements.

Therefore, there is a need to have an easy yet effective way to perform scanning apparatuses check-up and related services.

SUMMARY

The above-mentioned shortcomings, disadvantages and problems are addressed herein which will be understood by reading and understanding the following specification. Specifically, the present disclosure outlines a very simple and effective method and apparatus to perform mechanical condition check-up for QCS scanning apparatuses while the scanning apparatuses are either in operation with running sheet-making machines or idle while machine is shut for maintenance.

According to an aspect, a method for detecting a deflection or relative deflection between a source module and a detection module in a scanning apparatus and configured as a sensor pair for scanning transmission measurement of sheet material being transported in a machine direction through a sensing gap formed between the source module and the detection module is provided. The source module is arranged on a first side of the sensing gap and emits a sensing radiation or sensing energy radiation towards the sensing gap, and the detection module is arranged on a second side of the sensing gap opposite to the first side and detects the radiation from the source module and transmitted through the sensing gap. The method includes: attaching a removable blocking device to the detection module, so that a radiation-blocking area of the blocking device partially blocks, in an asymmetrical manner, a sub-area of the cross-sectional area of the radiation impinging onto a detection module aperture of the detection module; and performing a partially-blocked scanning process during which the source module and the detection module are jointly moved in a cross direction of the scanning apparatus, the source module emits the radiation and the detection module detects the radiation from the source module having transmitted through the sensing gap, whereby a selected portion of the radiation corresponding to the sub-area covered by the radiation-blocking area is blocked from being detected by the detection module aperture, whereby a partially-blocked sensor signal is obtained from the radiation detected by the detection module.

According to embodiments, the deflection is used for diagnostics of conditions of mechanical components or operations of the scanning apparatus, specifically for quantification of mechanical conditions, diagnostics or maintenance of scanning apparatus. For instance, the conditions of mechanical components or operations of the scanning apparatus include, but not limited to, any or all of the following attributes of a scanning apparatus mechanics: tension differential between lower drive belt and upper drive belt; phasing adjustment of lower drive pulley versus upper drive pulley; eccentricity of lower drive pulley or upper drive pulley; eccentricity of lower idler pulley or upper idler pulley; backlash between lower drive pulley and upper drive pulley; roundness of wheels on lower carriage and upper carriages; contact uniformity of wheels on guiderails; straightness, defects and debris on guiderails; fastening and alignment of source module and detection module onto their corresponding lower carriage and upper carriage; vibrations in the scanning apparatus mechanics caused by external excitation from other process machinery in the vicinity of the scanning apparatus; and vibrations in the scanning apparatus mechanics caused by internal excitation from any of the subsystems of the scanning apparatus mechanics.

According to embodiments, the method further includes: calculating the deflection between the source module and the detection module from the sensor signal obtained from the detection module is processed by a system for providing a partially-blocked scanning measurement as a function of cross direction position.

According to embodiments, in the calculating step, the deflection is calculated from the obtained partially-blocked scanning measurement by an algorithm to corresponding deflections, the algorithm being specifically based on at least one of a table, a linear-fit or a polynomial-fit.

According to embodiments, the calculating step provides a conversion from partially-blocked scanning measurement to the deflection profile in a unit of length.

According to embodiments, in the calculating step, the deflection is calculated from the partially-blocked scanning measurement and from a non-blocked scanning measurement obtained from a scanning process during which the blocking device is removed such as not to block a portion of the radiation.

According to embodiments, in the calculating step, the components relating to the actual sheet material are removed by an algorithm being typically based on at least one of a table, a linear fit or a polynomial fit.

According to embodiments, using the deflection profile for diagnostics of conditions of mechanical components or operations of the scanning apparatus, specifically for quantification of mechanical conditions, diagnostics or maintenance of scanning apparatus, includes extracting deflection characteristics from the deflection profile and associating the extracted deflection characteristics with the conditions of mechanical components or operations of the scanning apparatus specifically for quantification of mechanical conditions, diagnostics or maintenance of scanning apparatus.

According to an embodiment, in the extracting and associating step, power spectra are obtained from the deflection profile for forward and reverse scan directions. For instance, the deflection characteristics includes a deflection difference between the forward and reverse scan directions and/or a high frequency oscillation occurring at certain sections of the cross direction during the forward and reverse scan directions.

According to embodiments, the deflection characteristics includes a pair of steps or spikes at fixed positions in cross direction, a slope in the cross direction of the deflection profile, an oscillation of the deflection profile, a high frequency oscillation with beating amplitude of the deflection profile, a high frequency oscillation with multiple harmonics associated to the same primary frequency of the deflection profile, and/or an uneven variation of the deflection profile.

According to embodiments, the asymmetric partially blocking area of the blocking device is arranged to make the measurement signal primarily sensitive to deflections in the machine direction. For instance, the blocking area of the blocking device can be configured to block opposing halves of detection module aperture in a downstream machine direction and a upstream machine direction, and wherein the averaged deflection in machine direction is calculated from the difference between the mean values of the deflection profiles of the detection module aperture blocked in the downstream machine direction and the upstream machine direction.

According to embodiments, the asymmetric partially blocking area of the blocking device is arranged to make the measurement signal primarily sensitive to deflections in the cross direction. For instance, blocking area of the blocking device can be configured to block opposing halves of the detection module aperture in a back cross direction and a front cross direction, and wherein the deflection in cross direction is calculated from a difference between the mean values of the deflection profiles of the detection module aperture blocked in the back cross direction and the front cross direction.

According to embodiments, multiple passes of the partially-blocked scanning process are performed, wherein the radiation-blocking area of the blocking device is turned by a predetermined angle after a number of scans of the partially-blocked scanning process in order to separately evaluate deflections in both machine direction and cross direction.

According to embodiments, the scanning process is performed with moving sheet material in the sensing gap between the source module and the detection module.

According to embodiments, the scanning process is performed in absence of any moving sheet material in the sensing gap between the source module and the detection module.

According to embodiments, the radiation-blocking area of the blocking device has a straight edge in the cross-sectional area of the radiation, so that the sub-area covered by the radiation-blocking area extends from one side to the straight edge, whereas the other side of the straight edge is unobstructed by the radiation-blocking material. Specifically, the straight edge of the radiation-blocking area can be arranged according to at least one of a to c: a) the straight edge extends through the entire cross-sectional area of the radiation, b) the straight edge includes the centrum of the cross-sectional area of the radiation, and c) the straight edge extends along the machine direction or the cross direction.

According to a further aspect, a scanning apparatus being configured for scanning transmission measurement of sheet material being transported in a machine direction through a sensing gap of the scanning apparatus is provided. The scanning apparatus includes: a source module being arranged on a first side of the sensing gap and configured to emit a sensing radiation towards the sensing gap; a detection module being arranged on a second side of the sensing gap opposite to the first side and configured to detect the radiation from the source module and transmitted through the sensing gap; and a blocking device temporarily attached to the detection module, so that a radiation-blocking area of the blocking device in an asymmetrical manner partially blocks a sub-area of the transverse cross-sectional area of the radiation impinging onto a detection module aperture of the detection module. The source module and the detection module are configured to be jointly moved in the cross direction of the scanning apparatus to detect a deflection or relative of the source module and the detection module, specifically with the affixed blocking device.

According to embodiments, the radiation-blocking area of the blocking device has a straight edge in the transverse cross-sectional area of the radiation, so that the sub-area covered by the radiation-blocking area extends from the edge of detector window to the straight edge, whereas the other side of the straight edge is unobstructed by the radiation-blocking material. Specifically, the straight edge of the radiation-blocking area can be arranged according to at least one of a to c: a) the straight edge extends through the entire cross-sectional area of the radiation, b) the straight edge includes the centrum of the cross-sectional area of the radiation, and c) the straight edge extends along the machine direction or the cross direction.

According to embodiments, the blocking device is configured to block half of the radiation reaching the detection module aperture.

According to embodiments, the blocking area of the blocking device is configured to block a different half of detection module aperture in upstream machine direction, downstream machine direction, back cross direction and front cross direction.

According to a further aspect, a use of a blocking device for detecting a deflection of a scanning apparatus configured for scanning transmission measurement of sheet material being transported in a machine direction through a sensing gap formed between a source module and a detection module of the scanning apparatus from a partially-blocked sensor signal obtained from a partially-blocked scanning process is provided. The source module is arranged on a first side of the sensing gap and emits a scanning radiation towards the sensing gap, and the detection module is arranged on a second side of the sensing gap opposite to the first side and detects the radiation from the source module and transmitted through the sensing gap. During the partially-blocked scanning process the source module and the detection module being jointly moved in a cross direction of the scanning apparatus, the source module emits the radiation and the detection module detects the radiation from the source module having transmitted through the sensing gap, whereby a selected portion of the radiation corresponding to the sub-area covered by the radiation-blocking area is blocked from reaching the detection module, whereby the partially-blocked sensor signal is obtained from the radiation detected by the detection module.

According to a further aspect, using a blocking device on a scanning apparatus to generate a partially-blocked sensor signal and subsequently scanning measurement as indicative of a deflection or relative deflection between a source module and a detection module is provided. The deflection is used for diagnostics of conditions of mechanical components or operations of the scanning apparatus, specifically for quantification of mechanical conditions, diagnostics or maintenance of scanning apparatus, including, but not limited to, any or all of the following attributes of a scanning apparatus mechanics: tension differential between lower drive belt and upper drive belt; phasing adjustment of lower drive pulley versus upper drive pulley; eccentricity of lower drive pulley or upper drive pulley; eccentricity of lower idler pulley or upper idler pulley; backlash between lower drive pulley and upper drive pulley; roundness of wheels on lower carriage and upper carriages; contact uniformity of wheels on guiderails; straightness, defects and debris on guiderails; fastening and alignment of source module and detection module onto their corresponding lower carriage and upper carriage; vibrations in the scanning apparatus mechanics caused by external excitation from other process machinery in the vicinity of the scanning apparatus; and vibrations in the scanning apparatus mechanics caused by internal excitation from any of the subsystems of the scanning apparatus mechanics.

Embodiments are also directed at apparatuses for carrying out the disclosed methods and include apparatus parts for performing each described method aspect. These method aspects may be performed by way of hardware components, a computer programmed by appropriate software, by any combination of the two or in any other manner. Furthermore, embodiments according to the disclosure are also directed at methods for operating the described apparatus. The methods for operating the described apparatus include method aspects for carrying out functions of the apparatus.

BRIEF DESCRIPTION OF THE DRAWINGS

So that the manner in which the above recited features of the present disclosure can be understood in detail, a more particular description of the disclosure, briefly summarized above, may be had by reference to embodiments. The accompanying drawings relate to embodiments of the disclosure and are described in the following:

FIG. 22 shows an example of Root Cause Analysis (RCA) table and recommended actions according to embodiments.

DETAILED DESCRIPTION

Figure 1:
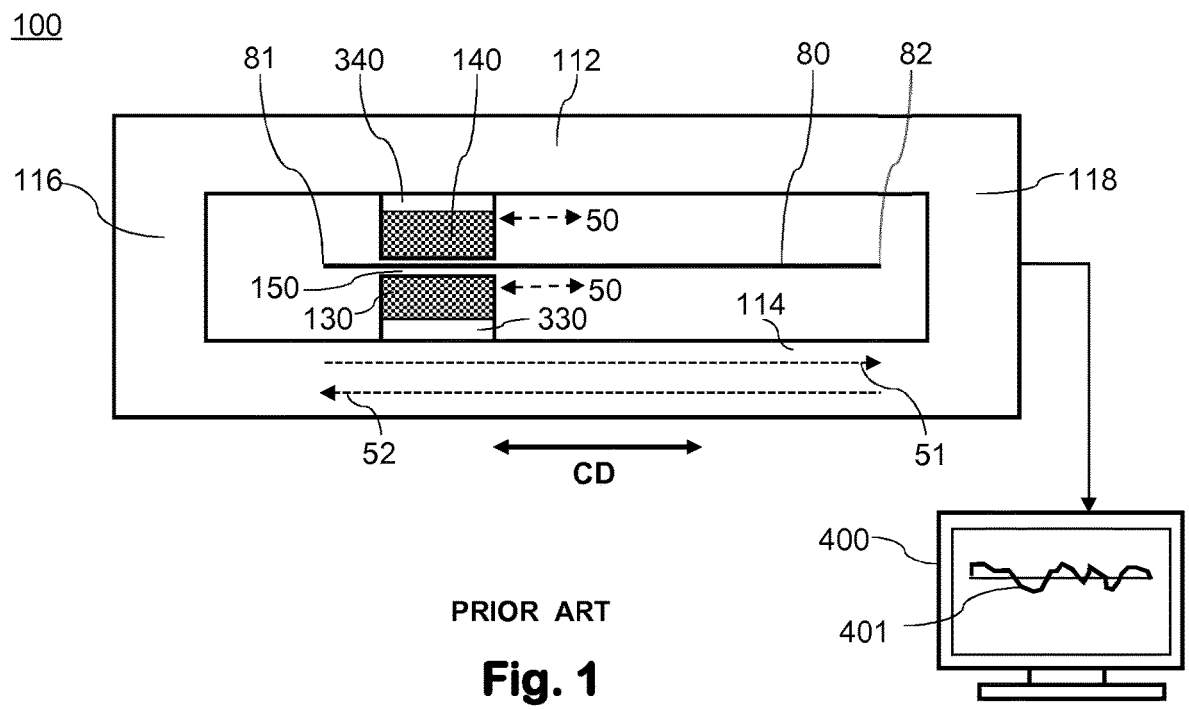
FIG. 1 shows a schematic elevation view of a scanning apparatus.

Reference will now be made in detail to the various embodiments of the disclosure, one or more examples of which are illustrated in the figures. Within the following description of the drawings, the same reference numbers refer to same components. Typically, only the differences with respect to individual embodiments are described. Each example is provided by way of explanation of the disclosure and is not meant as a limitation of the disclosure. Further, features illustrated or described as part of one embodiment can be used on or in conjunction with other embodiments to yield yet a further embodiment. It is intended that the description includes such modifications and variations Online scanning basis weight measurement utilizing beta rays, also known as "beta gauge", is a standard equipment on sheet material production processes like papermaking. A QCS scanning apparatus, such as the scanning apparatus 100, is typically a rectangle frame with a scanning beta gauge to measure the moving sheet material 80 that is produced by a process continuously. The scanning apparatus 100, specifically a beta gauge as part of the scanning apparatus 100, includes a source module 130 and a detection module 140 configured as a sensor pair for scanning transmission measurement of sheet material 80 being transported in a machine direction MD through a sensing gap 150 formed between the source module 130 and the detection module 140. The source module 130 is arranged on a first side of the sensing gap 150 and emits a sensing radiation R or sensing energy radiation R towards the sensing gap 150.

The detection module 140 is arranged on a second side of the sensing gap 150 opposite to the first side and detects the radiation R from the source module 130 and transmitted through the sensing gap 150. If a sheet material 80 is present in the sensing gap 150, the radiation R transmitted through the sensing gap 150 can be attenuated by the sheet material 80. The attenuation ratio is an indicative of the basis weight of the sheet material 80.

The source module 130 can be mounted on a first or lower carriage 330. The detection module 140 can be mounted on a second or upper carriage 340. In the context of the present disclosure, "upper" and "lower" can be understood with regard to an orientation depicted in the attached figures for ease of reference. However, in practice, parts being denoted or shown as being "upper" can be arranged lower than other corresponding parts being described as "lower", and vice versa. For instance, albeit the source module 130 is described and shown herein as being mounted on the lower carriage 330 and the detection module 140 is described and shown herein as being mounted on the upper carriage 340, the source module 130 can however be mounted on an upper carriage and the detection module 140 can however be mounted on a lower carriage in practice.

Figure 2A:
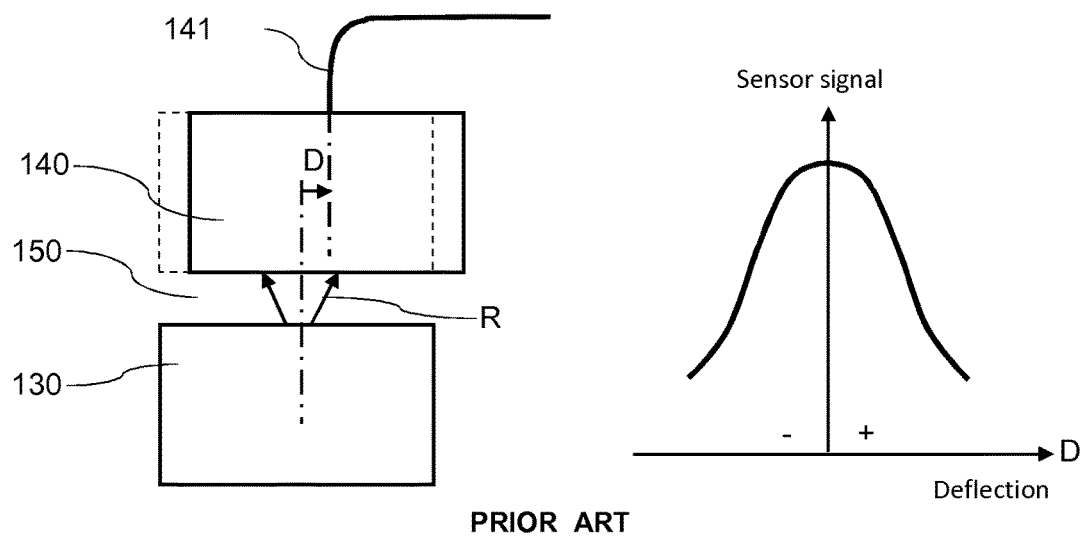
FIG. 2A shows a schematic view and a sensor signal graph illustrating a deflection between source module and a detection module of a scanning apparatus.

The source module 130 and the detection module 140, specifically being mounted on the separate lower carriage 330 and the upper carriage 340, can pose a challenge for maintaining accurate sheet measurement while these modules traverse across the sheet material. A relative motion of the source module 130 versus the detection module 140 can cause measurement inaccuracy. One part of this challenge can be solved by means of accurate mechanics of the scanning apparatus 100, and another part can be solved by designing the scanning apparatus 100 to be tolerant for a relatively small misalignment between the source module 130 and the detection module 140 to achieve minimal measurement error. The sensor pair comprised of source module 130 and detection module 140 on the scanning apparatus 100 has ideally a flat response for small deflections D between the centerlines of the source module 130 and the detection module 140, as shown in FIG. 2A. Hence, a direct measurement of the deflection D or relative deflection D between the source module 130 and the detection module 140 cannot be obtained by conventional scanning apparatuses.

The flat response of the scanning apparatus 100 in combination with a precise mechanical traversing structure provide accurate profile measurement of the sheet material 80. However, there are sometimes situations where the mechanical alignment accuracy during traversing needs to be diagnosed. This can be accomplished by means of mechanical or magnetic alignment sensors measuring relative motion between the source module 130 and the detection module 140. However, a large number of scanning apparatus 100 do not have such features available. The present disclosure overcomes this drawback by a simple passive blocking device 200 (see FIG. 2B and FIG. 3A) that can be temporarily, attached to the detection module 140, e.g., for using the scanning apparatus 100 for mechanical diagnostics purposes. The blocking device 200 can be made in form of a mask that blocks radiation R, e.g., for one half of a detection module aperture 142 from a center line of the detection module aperture 142, making the scanning apparatus 100 extremely sensitive to deflection D, such as a horizontal misalignment, and greatly overshadowing other radiation attenuating factors like the sheet basis weight. With detection module aperture 142 partially blocked, e.g., half-blocked, as shown in FIG. 4B or FIG. 4C, a sensor signal 141 obtained from the radiation R detected by the detection module 140 is indicative of deflection D, such as a relative horizontal head misalignment.

Accordingly, according to embodiments, a removable blocking device 200 is attached to the detection module 140, so that a radiation-blocking area 206 of the blocking device 200 partially blocks, in an asymmetrical manner, a sub-area of the cross-sectional area of the radiation R impinging onto a detection module aperture 142 of the detection module 140. Further, a partially-blocked scanning process is performed during which the source module 130 and the detection module 140 are jointly moved in a cross direction CD of the scanning apparatus 100, the source module 130 emits the radiation R and the detection module 140 detects the radiation R from the source module 130 having transmitted through the sensing gap 150, whereby a selected portion of the radiation R corresponding to the sub-area covered by the radiation-blocking area 206 is blocked from being detected by the detection module aperture 142, whereby a partially-blocked sensor signal 141 is obtained from the radiation R detected by the detection module 140.

That is, instead of adding a mechanical or magnetic alignment sensor, such as a dial indicator or hall-effect sensor, to detect a deflection D or relative deflection D in the scanning apparatus 100, the present disclosure utilizes existing sheet quality measuring scanning apparatuses to measure a deflection D of a scanning apparatus by partially blocking a sub-area of the cross-sectional area of the radiation R impinging onto a detection module aperture 142 of the detection module 140. These transmission-based scanning apparatuses are very common among all installed QCS systems. For transmission-based scanning apparatuses, a constant source signal is transmitted from the source module 130 through a moving sheet material 80 produced from a machine. This source signal is partially absorbed when it passes through the sheet material 80 and is detected by the detection module 140 arranged on the other side of the sensing gap 150. The reading of the detected sensor signal can thus be used to infer sheet quality measurements and variations. Although the embodiment is illustrated with a beta-ray basis weight sensor, the disclosed embodiments are suitable for and/or configured for other sheet property transmission sensors, including but not limited to, x-ray ash sensors, optical sensors, radio frequency sensors, microwave sensors, ultrasonic sensors and infrared moisture or weight sensors. The source signals of these scanning apparatuses typically radiate through a, e.g., circular, source module aperture from the source module 130. After these source signals transmit through the sheet material 80, an absorbed signal is detected through a, e.g., circular, detection module aperture 142 of the detection module 140. The source module aperture and the detection module aperture 142 together with other internal geometry designs can minimize the measurement sensitivity to deflections D between the source module 130 and the detection module 140.

Figure 2B:
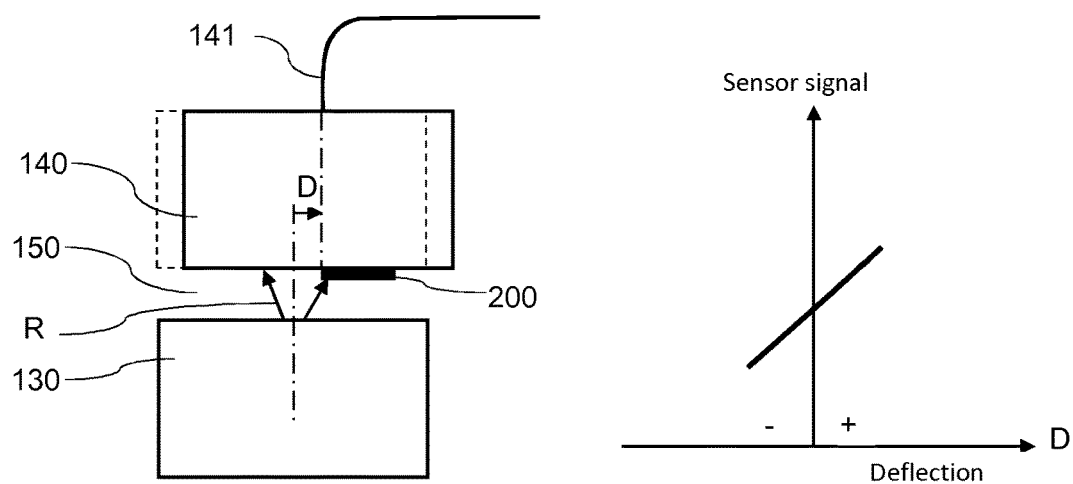
FIG. 2B shows a schematic view and a sensor signal graph illustrating a deflection between source module and a detection module of a scanning apparatus according to embodiments.

As outlined above, according to embodiments, as opposed to a normal operation of the scanning apparatus, a sub-area of the cross-sectional area of the radiation R impinging onto the detection module aperture 142 of the detection module 140 is partially blocked by the blocking device 200 to maximize the deflection sensitivity of existing scanning apparatuses 100 (see FIG. 2B).

Figure 3A:
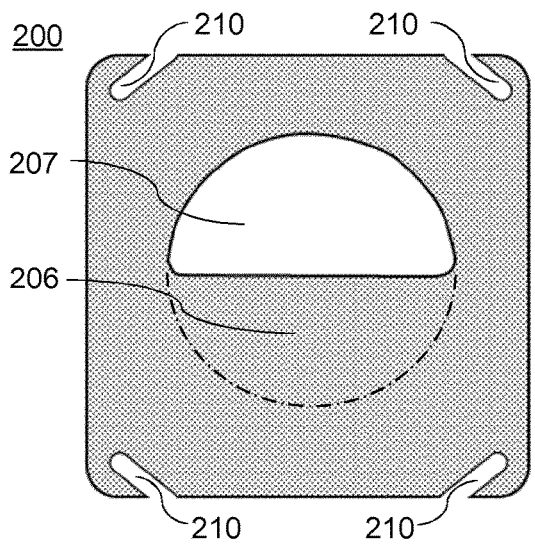
FIGS. 3A and 3B show schematic top views of blocking devices according to embodiments.
Figure 3B:
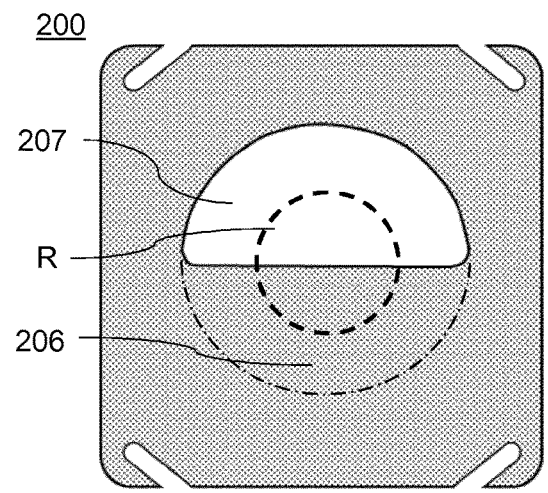

FIGS. 3A and 3B show schematic planar views of blocking devices 200 according to embodiments.

As shown in FIGS. 3A and 3B, the radiation-blocking area 206 of the blocking device can block a half or substantially a half of the detection module aperture 142. Specifically, the blocking device 200 can configured to block half of the radiation R reaching the detection module aperture 142. According to embodiments, the radiation-blocking area 206 of the blocking device can have a straight edge in the cross-sectional area of the radiation R, so that the sub-area covered by the radiation-blocking area 206 can extend from one side to the straight edge, whereas the other side of the straight edge is unobstructed by the radiation-blocking material. Further, the straight edge of the radiation-blocking area can be arranged according to at least one a to c: a) the straight edge extends through the entire cross-sectional area of the radiation R, b) the straight edge includes the centrum of the cross-sectional area of the radiation R, and c) the straight edge extends along the machine direction MD or the cross direction CD. For instance, a half circle plate, also known as "Half Measurement Plate (HMP)", can be used as blocking device 200.

Further, the blocking device 200 can include a blocking device aperture area 207 that is free from radiation-blocking material. The radiation R can reach the detection module unblocked or substantially unblocked through the blocking device aperture area 207. Furthermore, the blocking device can include mounting elements 210 for removable mounting or attaching the blocking device 200 to the detection module 140.

Figure 4A:
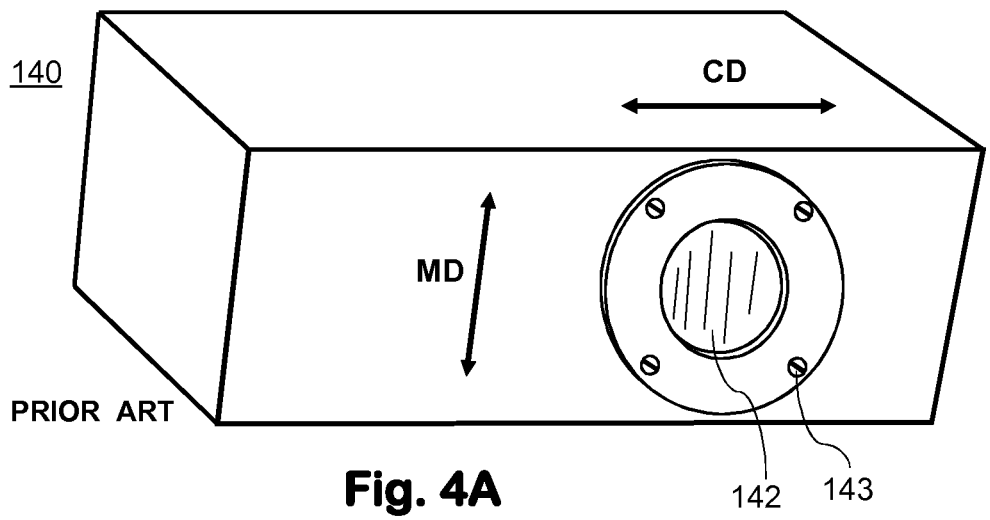
FIG. 4A shows a perspective view of a detection module of a scanning apparatus.
Figure 4B:
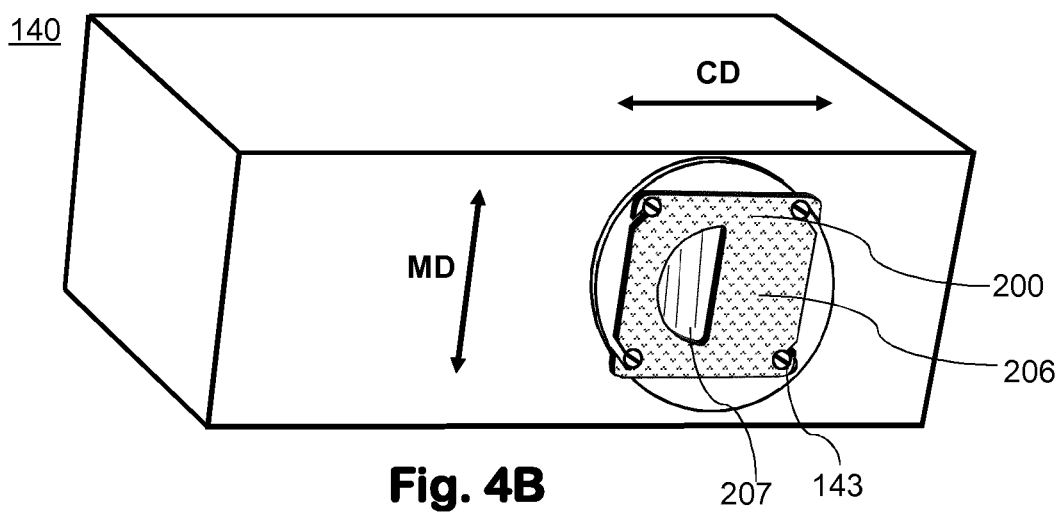
FIGS. 4B and 4C show perspective views of a detection module of a scanning apparatus according to embodiments.
Figure 4C:
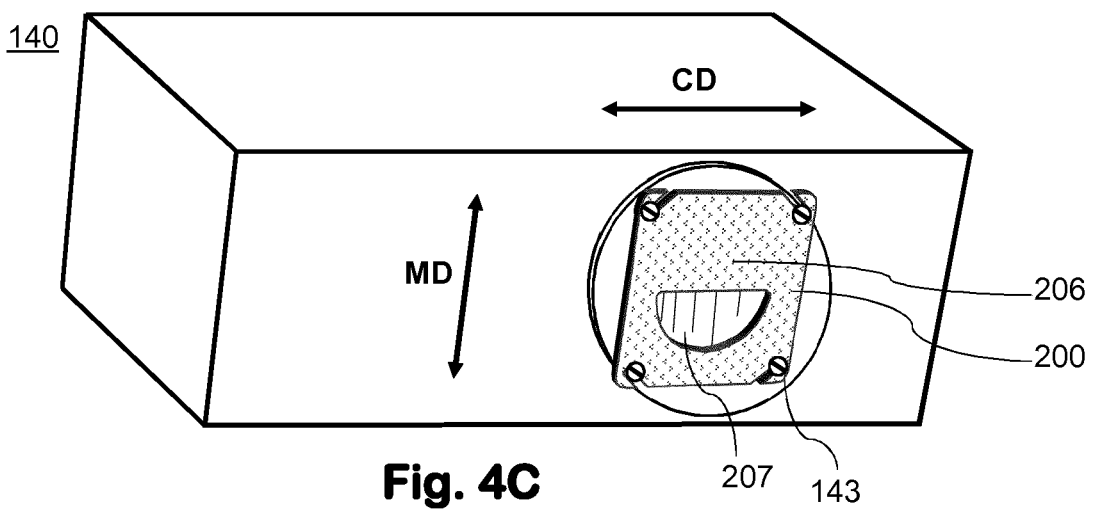

FIG. 4A shows the detection module 140 being not partially blocked by any blocking device. As can be seen from FIG. 4A, the detection module 140 includes the detection module aperture 142. The detection module aperture 142 can expose an area of the detection module 140 that is sensitive to the radiation R from the source module 130. The detection module aperture 142 usually includes radiation transparent windows for protection of internal components in detection module 140. The detection module 140, specifically the detection module aperture 142, can include detection module aperture screws 143. For instance, the detection module aperture 142 can be mounted to the detection module 140 by the detection module aperture screws 143.

According to embodiments, the asymmetric partially blocking area 206 of the blocking device 200 can be arranged to make the measurement signal 401 primarily sensitive to deflections D in the cross direction CD. Specifically, the blocking device 200 can be arranged so as to partially block, in an asymmetrical manner along the cross direction CD, a sub-area of the cross-sectional area of the radiation R impinging onto a detection module aperture 142 of the detection module 140. As shown in FIG. 4B, the blocking device 200 can be arranged to block one half of the detection module aperture 142 by the radiation-blocking area 206 in the cross direction CD, whereas the other half of the detection module aperture 142 is exposed by the blocking device aperture area 207. For instance, the straight edge can be perpendicular to the cross direction CD. Further, blocking device 200 can be fixed to the detection module 140 by bringing the mounting elements 210 of the blocking device 200 in engagement with the detection module aperture screws 143.

According to embodiments, the asymmetric partially blocking area 206 of the blocking device 200 can be arranged to make the measurement signal 141 primarily sensitive to deflections D in the machine direction MD. Specifically, the blocking device 200 can be arranged so as to partially block, in an asymmetrical manner along the machine direction MD, a sub-area of the cross-sectional area of the radiation R impinging onto a detection module aperture 142 of the detection module 140. As shown in FIG.

4C, the blocking device 200 can be arranged to block one half of the detection module aperture 142 by the radiation-blocking area 206 in the machine direction MD, whereas the other half of the detection module aperture 142 is exposed by the blocking device aperture area 207. For instance, the straight edge can be perpendicular to the machine direction MD. Further, blocking device 200 can be fixed to the detection module 140 by bringing the mounting elements 210 of the blocking device 200 in engagement with the detection module aperture screws 143.

Figure 5:
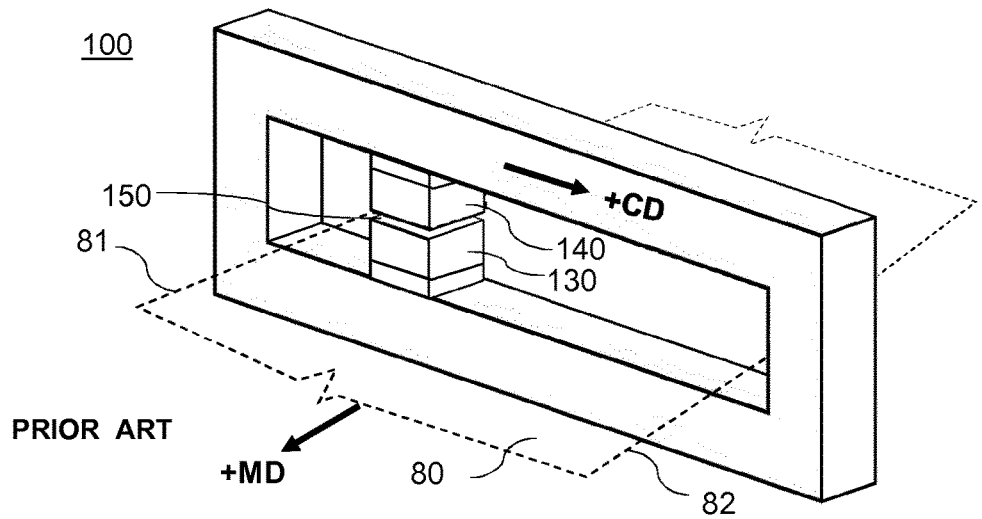
FIG. 5 shows a schematic perspective view of a scanning apparatus.
Figure 10:
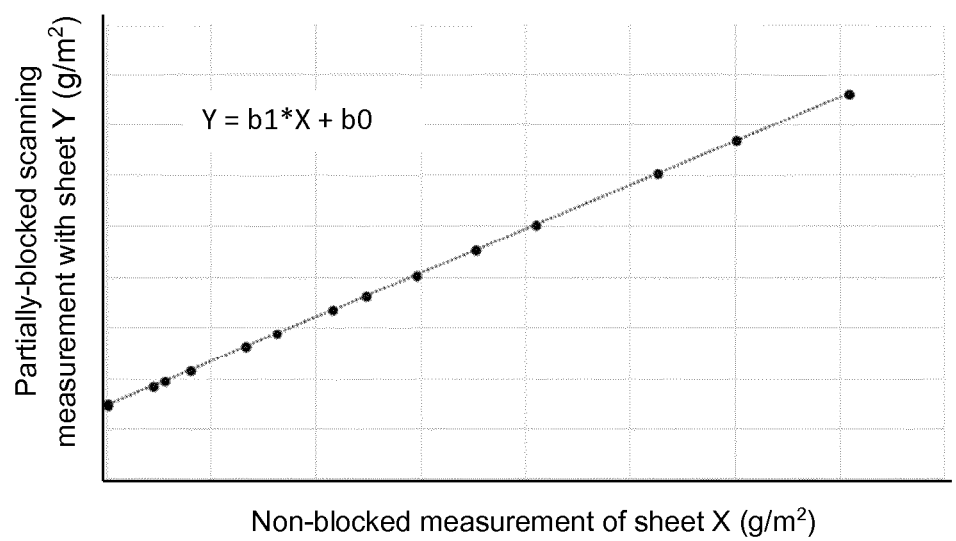
FIG. 10 shows a graph illustrating a relationship between the partially blocked scanning measurement and non-blocked measurement of sheet material according to embodiments.

FIG. 5 shows a perspective view of the scanning apparatus 100 with a sheet material 80 indicated by the dashed lines. According to embodiments, the scanning process can be performed with moving sheet material 80 in the sensing gap 150 between the source module 130 and the detection module 140. The sheet material 80 can be moved in the machine direction MD, while the scanning process is performed by jointly moving the source module 130 and the detection module 140 in the cross direction CD. Specifically, the source module 130 and the detection module 140 can be moved back and forth 50 in the cross direction CD from a back sheet edge 81 to a front sheet edge 82. While a scanning apparatus 100 is actively used for production and the sheet-making process is in a steady-state condition, the quality control loops and reports can be temporarily suspended. Under these conditions, a blocking device 200 can be attached to the detection module 140 to measure both sheet property and deflection D simultaneously. In this situation, the steady-state sheet material property also need to be measured separately either before and/or after partially blocked measurements are taken. The steady-state sheet material property measurements can be proportionally removed from the measurements that are obtained with blocking device 200. An example of empirically derived relation between sheet basis weight measurements with and without the blocking device 200 in place is shown in FIG. 10. This relationship can be used to proportionally remove sheet basis weight measurement to obtain the partially-blocked scanning measurement without sheet basis weight measurement.

Figure 9:
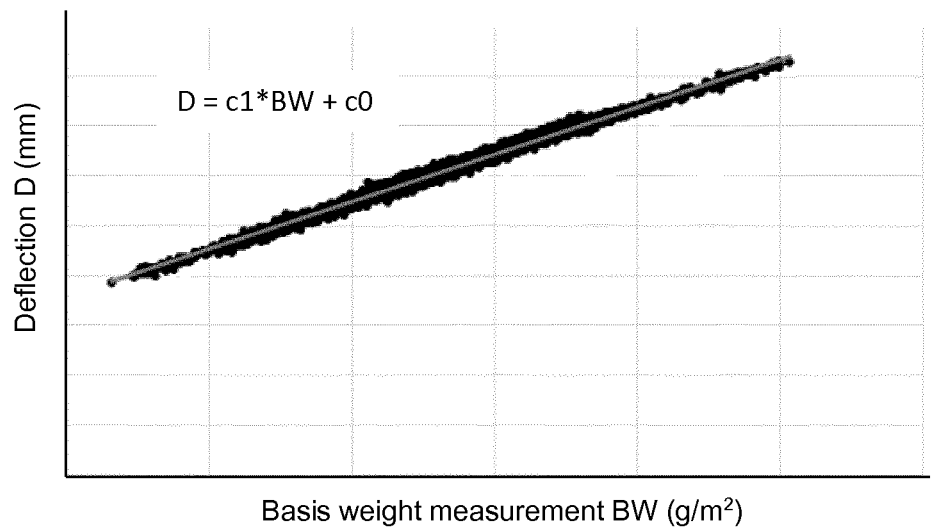
FIG. 9 shows a graph illustrating a relationship between the deflection of a scanner apparatus and its equivalent basis weight reading in $g/m^2$ according to embodiments.

A change of the partially-blocked scanning measurement 401 without sheet basis weight measurement is an indicative of a change of deflection D between the source module 130 and detection module 140. An example of the relationship between the measurements taken with a blocking device 200, versus deflection D measured by a calibrated deflection measurement instrument is shown in FIG. 9. It is noted that the partially-blocked scanning measurement with the blocking device 200 can be sensitive to small change of the deflection D between the source module 130 and the detection module 140. An example of the slope between the change of partially-blocked scanning measurement 401 obtained with the blocking device 200 and the change of the deflection D is about 45 (g/m$^2$)/mm, with this relation nearly linear over typical range of scanning apparatus mechanical deflections. This relationship can be effectively used obtain deflection measurements while the scanning apparatus 100 is in operation. The tests performed in practice in accordance with embodiments has reliably detected changes of deflection D with a precision better than 10 micrometers (μm) on a 10 meter long scanning apparatus.

According to embodiments, the scanning process can be performed in absence of any moving sheet material 80 in the sensing gap 150 between the source module 130 and the detection module 140. While a scanning apparatus 100 is not in use for production (such as machine shut-down for maintenance), the blocking device 200 can be mounted and measure deflections D without sheet material in the sensing gap 150 between the source module 130 and the detection module 140. Under this condition, the measured readings can be directly converted in the mechanical deflections in mm or other length units.

Figure 6A:
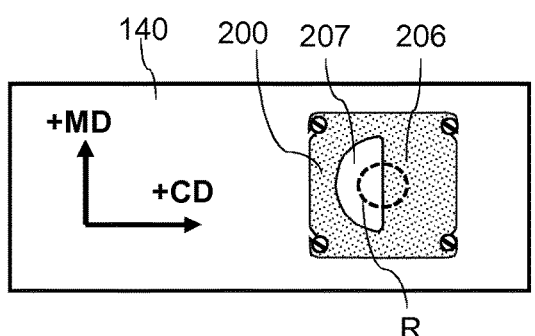
FIGS. 6A to 6D show schematic views of blocking devices according to embodiments.
Figure 6B:
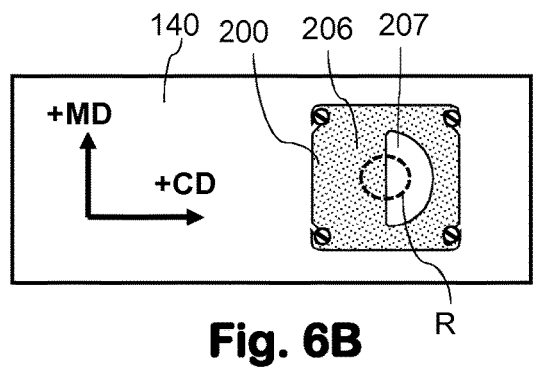

As shown in FIGS. 6A and 6B, the blocking area 206 of the blocking device 200 can be configured to block opposing halves of the detection module aperture 142 in a back cross direction CD− and a front cross direction CD+. The averaged deflection D in cross direction CD can then be calculated from a difference between the mean values of the partially-blocked scanning measurement 401 of the detection module aperture 142 blocked in the back cross direction CD− and the front cross direction CD+. According to embodiments, the averaged deflection D in cross direction CD can be a persistent offset.

Figure 6C:
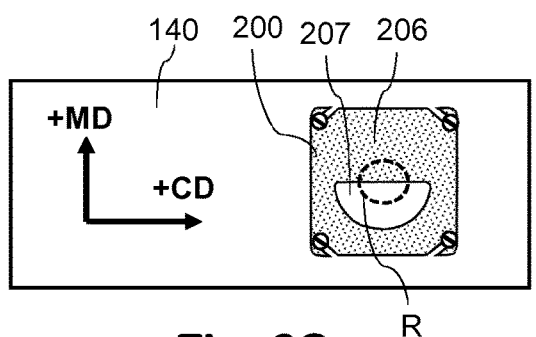
Figure 6D:
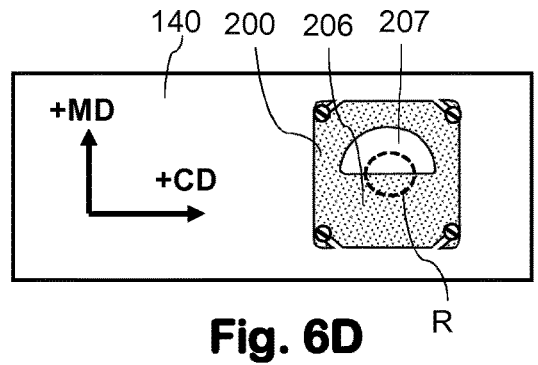

As shown in FIGS. 6C and 6D, the blocking area 206 of the blocking device 200 can be configured to block opposing halves of detection module aperture 142 in a downstream machine direction MD− and an upstream machine direction MD+. The averaged deflection D in machine direction MD can then be calculated from the difference between the mean values of the partially-blocked scanning measurement 401 of the detection module aperture 142 blocked in the downstream machine direction MD− and the upstream machine direction MD+. According to embodiments, the averaged deflection D in machine direction MD can be a persistent offset.

Further, the blocking area 206 of the blocking device 200 is configured to block a different half of detection module aperture 142 in upstream machine direction MD−, downstream machine direction MD+, back cross direction CD− and front cross direction CD+. Specifically, by arranging the blocking device 200 or more than one blocking devices 200 in four different blocking orientations (as shown in FIGS. 6A to 6D) and setting the scanning apparatus 100 to scan back and forth, the deflections D in both machine direction MD and cross direction CD along the entire width of the scanning apparatus 100 can be completely measured in practice.

According to embodiments, multiple passes of the partially-blocked scanning process can be performed, wherein the radiation-blocking area 206 of the blocking device 200 is turned by a predetermined angle after a number of scans of the partially-blocked scanning process in order to separately evaluate deflections D in both machine direction MD and cross direction CD.

Figure 7:
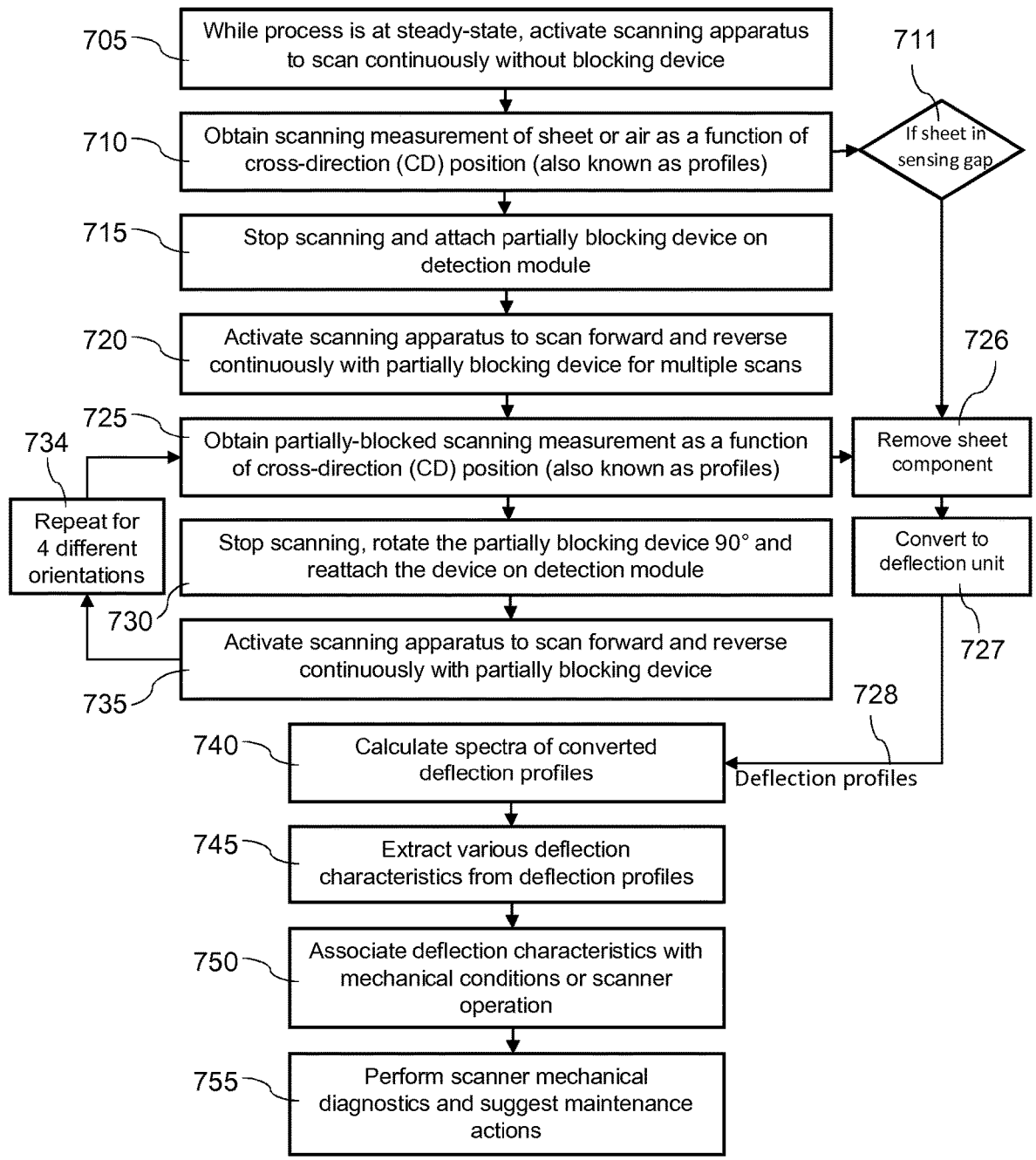
FIG. 7 shows a flow diagram of a method for detecting a deflection according to embodiments.

FIG. 7 shows a flow diagram of a method 700 for detecting a deflection D between a source module 130 and a detection module 140 in a scanning apparatus 100 according to embodiments. While FIG. 7 shows several method blocks embodiments described herein can include not all of these blocks or additional blocks not shown in FIG. 7.

In block 705, while the process is at steady-state, the scanning apparatus 100 can be activated to scan continuously without a blocking device 200 fixed to the detection module 140. In block 710 scanning measurements of sheet material 80 or air as a function of a cross direction CD position (also known as profiles) can be obtained. In block 715, scanning can be stopped and the blocking device 200 can be attached to the detection module 140. In block 720, the scanning apparatus 100 can be activated to scan forward and reverse continuously with the blocking device 200 attached to the detection module 140 for multiple scans. In block 725, partially-blocked scanning measurements as a function of the cross direction CD position can be obtained. In block 730, the scanning can be stopped and the blocking device 200 can be rotated by 90° and reattached to the detection module 140. In block 735, the scanning apparatus 100 can be activated again to scan forward and reverse continuously with blocking device 200 attached to the detection module 140. According to block 734, blocks 725, 730 and 735 can be repeated until partially-blocked scanning measurements for four different orientations of the blocking device 200 are obtained.

As indicated in block diagram FIG. 7, if sheet material 80 is present in the sensing gap 150 when the partially-blocked scanning measurements are obtained, the component of the sheet material 80 to the partially-blocked scanning measurements can be removed (see blocks 711 and 726). In block 727, the partially-blocked scanning measurements can be converted into deflection profiles 728. In block 740, spectra of the converted deflection profiles 728 can be calculated. In block 745, various deflection characteristics can be extracted from the converted deflection profiles 728. In block 750, the extracted deflection characteristics can be associated with mechanical conditions or scanner operations. In block 755, scanner mechanical diagnostics can be performed and maintenance actions can be conducted.

According to embodiments, the simplifications and deviations from the flow chart in FIG. 7 are not limited. For instance, the flow chart in FIG. 7 can be simplified to get a rough estimate of gross deflection of the scanning apparatus 100 by taping a blocking material equivalent to the blocking device 200 onto the detection module to partially blocking the detection module aperture 142 for scanning only in one direction 51 with the sheet absent or present and/or the partially-blocked measurement can also be used directly in spectral calculation and measurement characteristics extraction without being converted in deflection units.

Figure 8:
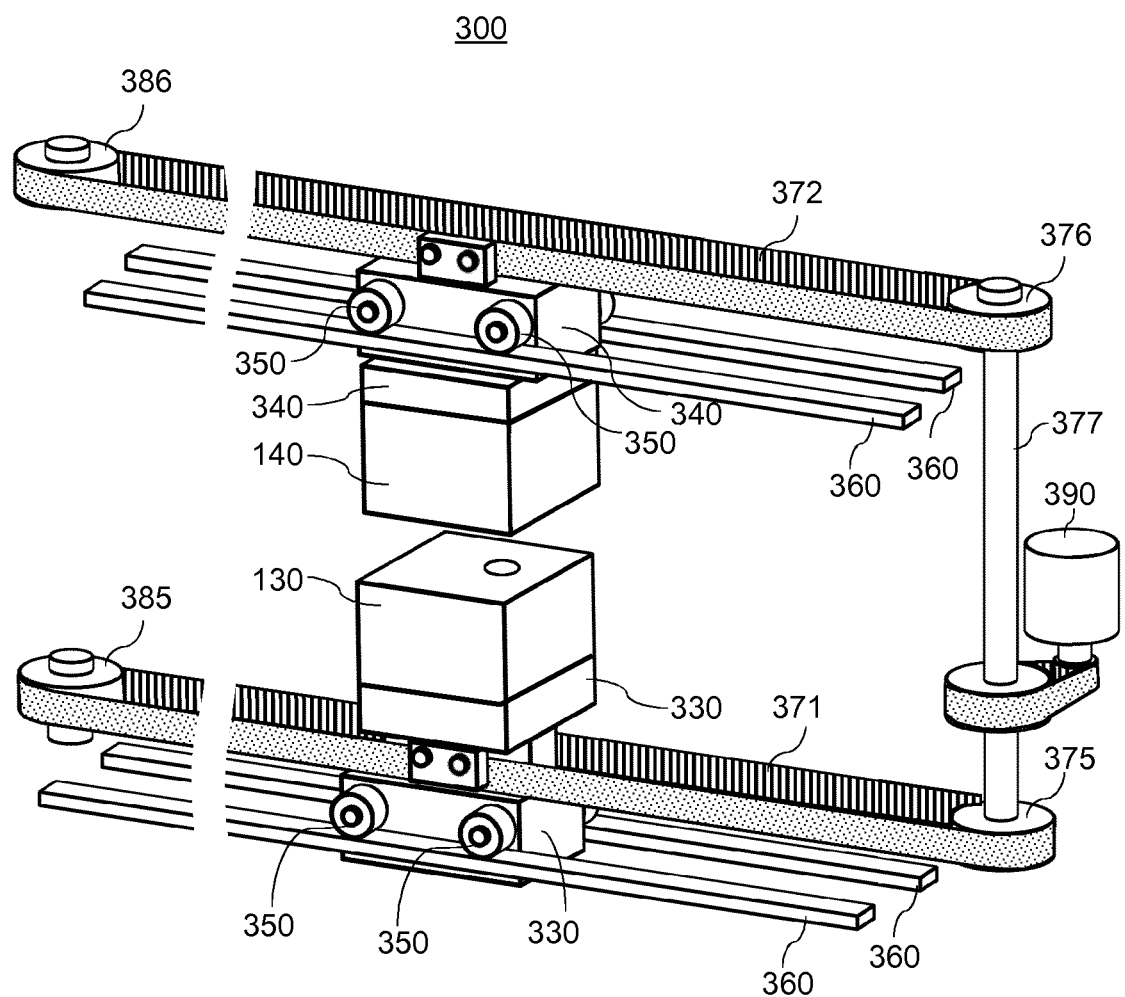
FIG. 8 shows a schematic view of a scanning apparatus internal mechanics.

FIG. 8 shows a schematic perspective view of the inner workings of a scanning apparatus 100 illustrating an example of, but not limited to, the scanning apparatus mechanics 300 according to embodiments. As shown in FIG. 8, the source module 130 can be provided on the lower carriage 330. The lower carriage 330 can include carriage wheels 350. The carriage wheels 350 can be in engagement with guiderails 360 for traversing the source module 130 back and forth. Further, the lower carriage 330 can be connected to a lower drive belt 371. The lower drive belt 371 can be connected to a lower drive pulley 375. The lower drive pulley 375 can be connected to a drive shaft 377 being connected to a drive motor 390 for driving the lower carriage 330 back and forth. Furthermore, the lower drive belt 371 can be connected to a lower idler pulley 385 opposite to the lower drive pulley 375.

Likewise, the detection module 140 can be provided on the upper carriage 340. The upper carriage 340 can include carriage wheels 350. The carriage wheels 350 can be in engagement with a guiderails 360 for traversing the detection module 140 back and forth. Further, the upper carriage 340 can be connected to an upper drive belt 372. The upper drive belt 372 can be connected to an upper drive pulley 376. The upper drive pulley 376 can be connected to the drive shaft 377 being connected to the drive motor 390 for driving the upper carriage 340 back and forth. Furthermore, the upper drive belt 372 can be connected to an upper idler pulley 386 opposite to the upper drive pulley 376.

According to embodiments, the deflection D can be used for diagnostics of conditions of mechanical components or operations of the scanning apparatus 100, specifically for quantification of mechanical conditions, diagnostics or maintenance of scanning apparatus 100. For instance, the conditions of mechanical components or operations of the scanning apparatus 100 include, but not limited to, any or all of the following attributes of a scanning apparatus mechanics 300:

a) tension differential between lower drive belt 371 and upper drive belt 372;
  b) phasing adjustment of lower drive pulley 375 versus upper drive pulley 376;
  c) eccentricity of lower drive pulley 375 or upper drive pulley 376;
  d) eccentricity of lower idler pulley 385 or upper idler pulley 386;
  e) backlash between lower drive pulley 375 and upper drive pulley 376;
  f) roundness of wheels 350 on lower carriage 330 and upper carriage 340;
  g) contact uniformity of wheels 350 on guiderails 360;
  h) straightness, defects and debris on guiderails 360;
  i) fastening and alignment of source module 130 and detection module 140 onto their corresponding lower carriage 330 and upper carriage 340;
  j) vibrations in the scanning apparatus mechanics 300 caused by external excitation from other process machinery in the vicinity of the scanning apparatus 100; and
  k) vibrations in the scanning apparatus mechanics 300 caused by internal excitation from any of the subsystems of the scanning apparatus mechanics 300.

Accordingly, when practicing embodiments a diagnostic of a malfunction of a scanning apparatus mechanics 300 can be given based on the measurement of the deflection D.

According to embodiments, the deflection D between the source module 130 and the detection module 140 is obtained from the detection module 140. Specifically, calculating the deflection D between the source module 130 and the detection module 140 from the sensor signal 141 obtained from the detection module 140 can be processed by a system 400 for providing a partially-blocked scanning measurement 401 as a function of cross direction CD position. Scanning measurement 401 is also known as profile. For instance, calculating the deflection can include unit conversion, e.g., from an equivalent unit in grams per square meter ($g/m^2$) to a unit of length in millimeter.

Based on experiments with many existing scanning apparatuses 100, it has been found that the actual scanner deflections are highly correlated with the measurements obtained from a transmission-based sensor that are covered with the blocking device. This correlation can be approximated by a linear or low-order polynomials. FIG. 9 illustrates the relationship between the deflection D of a scanning apparatus 100 and its equivalent sheet basis weight reading in $g/m^2$, i.e., the basis weight measurement BW. With a simple linear fitting, it yields a conversion factor of approximately 0.021~0.023 mm deflection per basis weight in $g/m^2$. Hence, the relationship between the deflection D and the basis weight measurement BW can be approximated by the following formula: $D=c1*BW+c0$. Accordingly, the partially-blocked sensor signal 141 or scanning measurement 401 can be converted into the actual mechanical deflection units.

According to embodiments, in the calculating step, the deflection D can be calculated from the obtained partially-blocked scanning measurement 401 by an algorithm to its corresponding deflections D. For instance, the algorithm can be based on at least one of a table, a linear-fit or a polynomial-fit. Specifically, the calculating step provides a conversion from partially-blocked sensor signal 141 or scanning measurement 401 to the deflection D in a unit of length.

According to embodiments, in the calculating step, the deflection D can be calculated from the partially-blocked scanning measurement 401 and from a non-blocked scanning measurement obtained from a scanning process during which the blocking device 200 is removed such as not to block a portion of the radiation R. For instance, in the calculating step, the components relating to the actual sheet material 80 can be removed by an algorithm being, e.g., based on at least one of a table, a linear fit or a polynomial fit.

FIG. 10 shows a graph illustrating a relationship between the partially blocked scanning measurement and non-blocked measurement of sheet material 80. In FIG. 10, the partially blocked scanning measurement while a sheet material is present in the sensing gap 150 is depicted on the Y-axis and the non-blocked measurement of sheet material 80 is depicted on the X-axis. The relationship between the partially blocked scanning measurement while a sheet material is present in the sensing gap 150 and non-blocked measurement of sheet material 80 can be approximated by the following linear fit: $Y = b1*X + b0$, where Y being the partially blocked scanning measurement while a sheet material is present in the sensing gap 150, X being non-blocked measurement of sheet material 80, b1 being the slope of the linear fit, and b0 being the offset of the linear fit.

As outlined above, using the deflection D as diagnostics of conditions of mechanical components or operations of the scanning apparatus, specifically for quantification of mechanical conditions, diagnostics or maintenance of scanning apparatus, can include extracting deflection characteristics from either the partially-blocked scanning measurement 401 or the converted deflection profile 728. That is, analysis can be performed on the either partially-blocked scanning measurement 401 or the converted deflection profile 728 and characteristic of the deflection profile 728 can be extracted as deflection characteristics. The extracted deflection characteristics can be associated with the conditions of mechanical components or operations of the scanning apparatus, specifically for quantification of mechanical conditions, diagnostics or maintenance of scanning apparatus. For instance, a specific measurement characteristic can be extracted from the partially-blocked scanning measurement 401 and associated to one or more attributes of the scanning apparatus mechanics 300. Further, measurement characteristics of the partially-blocked scanning measurement 401 can be extracted, too, to be associated with the conditions of mechanical components or operations of the scanning apparatus, however for qualification of mechanical conditions, diagnostics or maintenance of scanning apparatus.

Further, power spectra can be obtained from the deflection profiles 728 for forward and reverse scan directions. For instance, the deflection characteristics can include a deflection difference between the forward and reverse scan directions. Additionally or alternatively, the deflection characteristics can include a high frequency oscillation occurring at certain sections of the cross direction CD during the forward and reverse scan directions.

Figure 11:
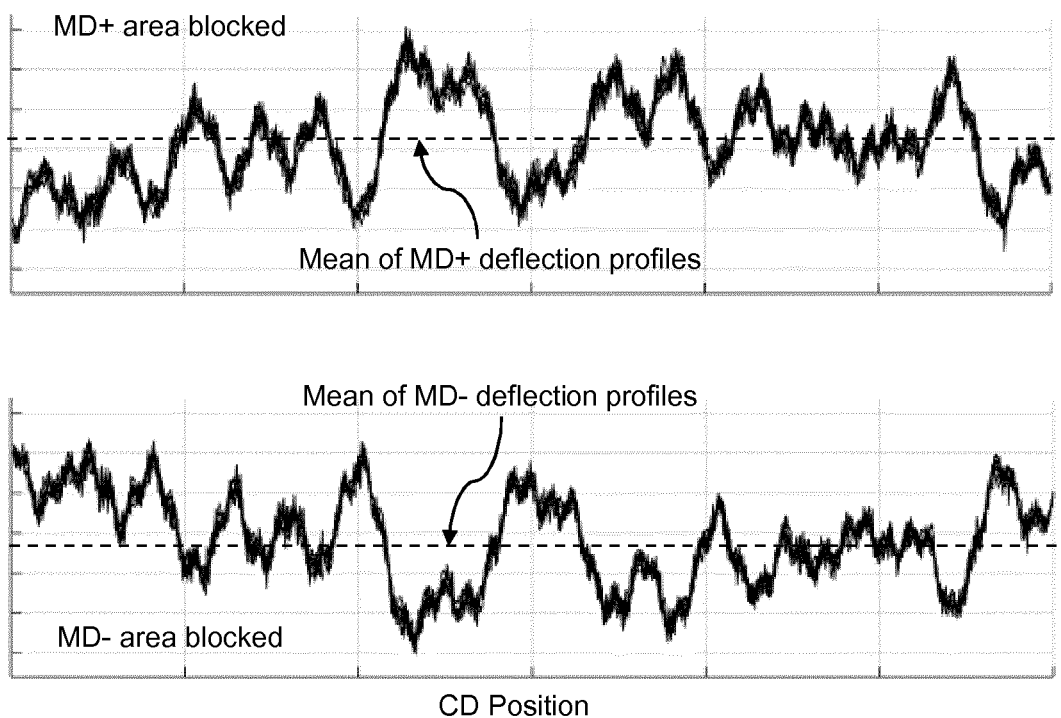
FIG. 11 shows graphs illustrating deflection profiles of partially-blocked measurements being performed with the blocking device being arranged so as to block opposing halves in the machine direction according to embodiments.

FIG. 11 shows graphs illustrating deflection profiles of partially-blocked measurements being performed with the blocking device 200 being arranged so as to block opposing halves in the machine direction MD as it is exemplary shown in FIGS. 6C and 6D.

If there is a persistent offset between the source module 130 and the detection module 140, then the partially blocked scanning signal 141 from these two opposing half-blocked configurations may have different mean values. The half of the difference between these two mean values can be an indication of the, specifically persistent, offset between the source module 130 and the detection module 140. That is, the deflection characteristics extracted from the deflection profile 728 can include a difference in the mean values of partially blocked measurements performed with the upstream machine direction MD+ and the downstream machine direction MD− blocked, respectively. And the associated condition can be a misalignment between the lower carriage 330 of the source module 130 and the upper carriage 340 of the detection module 140 in machine direction MD. If this misalignment or offset is greater than a specification, then the lower carriage 330 of the source module 130 and/or of the upper carriage 340 of the detection module 140 may be re-aligned.

Likewise, an offset between the source module 130 and the detection module 140 in cross direction can be assessed by blocking respective sides of the detection module aperture 142 in back cross direction CD− and front cross direction CD+, respectively, as it is shown in FIGS. 6A and 6B.

Figure 12:
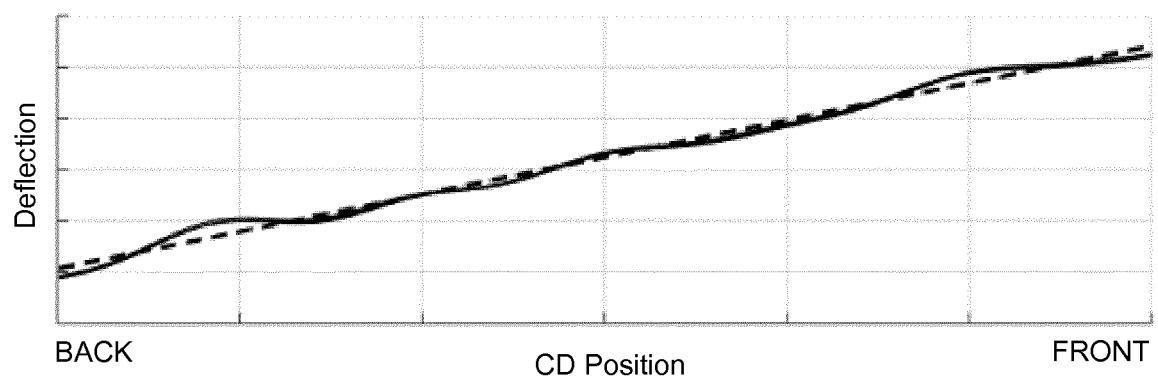
FIG. 12 shows a graph illustrating a deflection profile that is monotonically sloping according to embodiments.

FIG. 12 shows a graph illustrating a deflection profile that is monotonically sloping. The mechanical offset between the source module 130 and the detection module 140 may gradually change as the source module 130 and the detection module 140 traverse from one side to another. The gradually increase or decrease in the offset can be determined from the slope of the deflection profile 728 of the partially-blocked measurement data. Accordingly, the extracted deflection characteristics can include a slope, specifically a monotone slope, in cross direction. The slope of deflection profile 728 is the indication of this uneven offset between the source module 130 and the detection module 140 as the upper and lower carriages 330, 340 scan from one end of scanner apparatus 100 to the other end. The uneven offset often come from an uneven belt tension between the lower drive belt 371 and the upper drive belt 372. Accordingly, the associated condition can be a tension differential between the lower drive belt 371 and the upper drive belt 372. Such an uneven offset can be corrected in practice by adjusting the belt tension.

Figure 13:
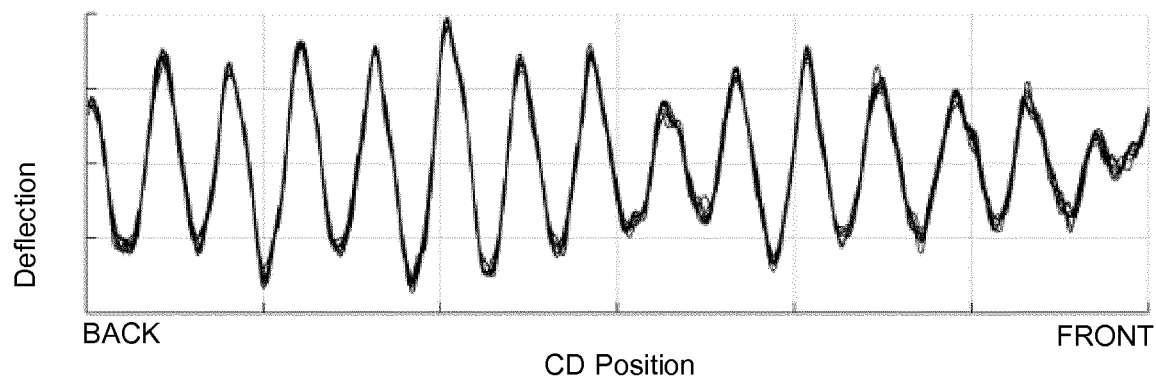
FIG. 13 shows a graph illustrating an oscillating deflection profile according to embodiments.

FIG. 13 shows a graph illustrating an oscillating CD deflection profile with a specific dominant wavelength. The deflection profile 728 obtained from the partially-blocked measurement 401 may exhibit sinusoidal oscillations. If the wavelength of the oscillation matches with the circumference of rotating mechanical parts such as pulleys (e.g., the lower drive pulley 375, the upper drive pulley 376, the lower idle pulley 385, and/or the upper drive pulley 386) or wheels (e.g., carriage wheels 350), then the oscillation of the deflection D can be an indication that these mechanical parts are either faulty or unevenly worn. For instance, the extracted deflection characteristics is an oscillation of the deflection profile 728 as shown in FIG. 13, the associated condition can be an eccentricity of the lower drive pulley 375 or the upper drive pulley 376, an eccentricity of the lower idler pulley 385 or the upper idler pulley 386, an eccentricity mismatch between the lower drive pulley 375 and the upper drive pulley 376, and/or uneven roundness of the pulleys.

Figure 14:
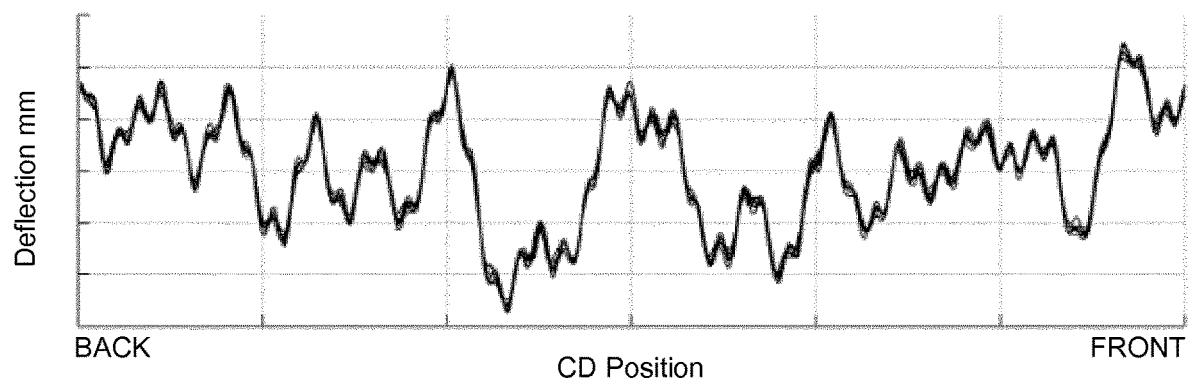
FIG. 14 shows a graph illustrating a medium frequency machine direction MD deflection profile according to embodiments.

FIG. 14 shows a graph illustrating a medium frequency machine direction MD deflection profile with not a single dominant oscillation. The partially-blocked scanning measurement 401 obtained from the partially-blocked sensor signal 141 may exhibit uneven variations but not a single dominant oscillatory as shown in FIG. 14. Accordingly, the extracted deflection characteristics can include a medium frequency when the blocking device 200 is arranged so as to partially block the detection module aperture 142 in the machine direction MD. This type of deflection variation may indicate that an alignment of the carriage wheels 350 on the guiderails 360 that guides the movement of the upper carriage 330 and the lower carriage 340 is not perfectly straight. Accordingly, the associated condition can be a misalignment of the carriage wheels 350, a misalignment of guiderails 360, and/or uneven contact between the carriage wheels 350 and the guiderails 360. Specifically, the distances between the local max and min points may match with the distance between the guiderail alignment adjusters provided to the lower carriage 330 and/or upper carriage 350. By adjusting the alignment adjusters, such deflection variations can be altered or reduced in practice.

Figure 15:
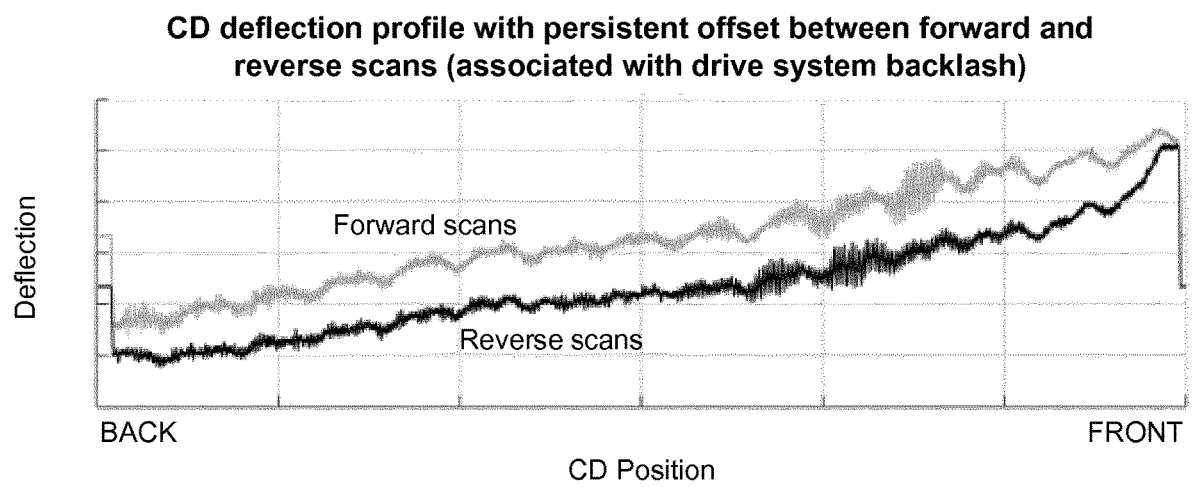
FIG. 15 shows a graph illustrating deflection profile with persistent offset between forward and reverse scans according to embodiments.

FIG. 15 shows a graph illustrating deflection profile with persistent offset between forward and reverse scans. The deflection profile 728 can be obtained when the blocking device 200 is arranged so as to partially block the detection module aperture 142 in the cross direction CD. As the scanning apparatus 100 traverses back and forth, the partially-blocked scanning measurement 401 obtained from forward movement may not be the same as that from reverse movement. Accordingly, the extracted deflection characteristics can include a deflection offset between forward and reverse movement. The deflection offset between forward and reverse movement may be associated with the condition of hysteresis or backlash of the scanning apparatus 100 moving mechanism, or by not all carriage wheels being in contact with the guiderails. In practice, by removing hysteresis or backlash, the forward and reverse deflection offset will be reduced. FIG. 15 shows an example of forward to reverse offset caused by backlash of the drive shaft 377.

Figure 16:
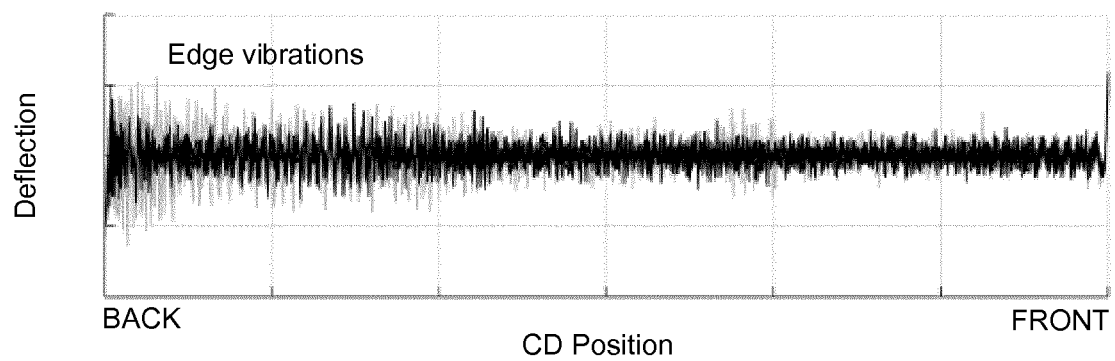
FIG. 16 shows a graph illustrating a high frequency CD deflection profile near edges according to embodiments.

FIG. 16 shows a graph illustrating a high frequency CD deflection variation near back edge. The deflection profile can be obtained when the blocking device 200 is arranged so as to partially block the detection module aperture 142 in the cross direction CD. As the scanning apparatus 100 traverses back and forth, the partially-blocked scanning measurement 401 obtained from the partially blocked sensor signal 141 may exhibit some high frequency oscillations at, specifically only at, certain CD positions. Accordingly, the extracted deflection characteristics can include high frequency oscillations at, specifically only at, certain CD positions. The wavelength of such high frequency variations may be associated with a component length of some moving parts such as cable chains. FIG. 16 shows an example of the vibrations occur near back edge by the movement of a cable chain.

Figure 17:
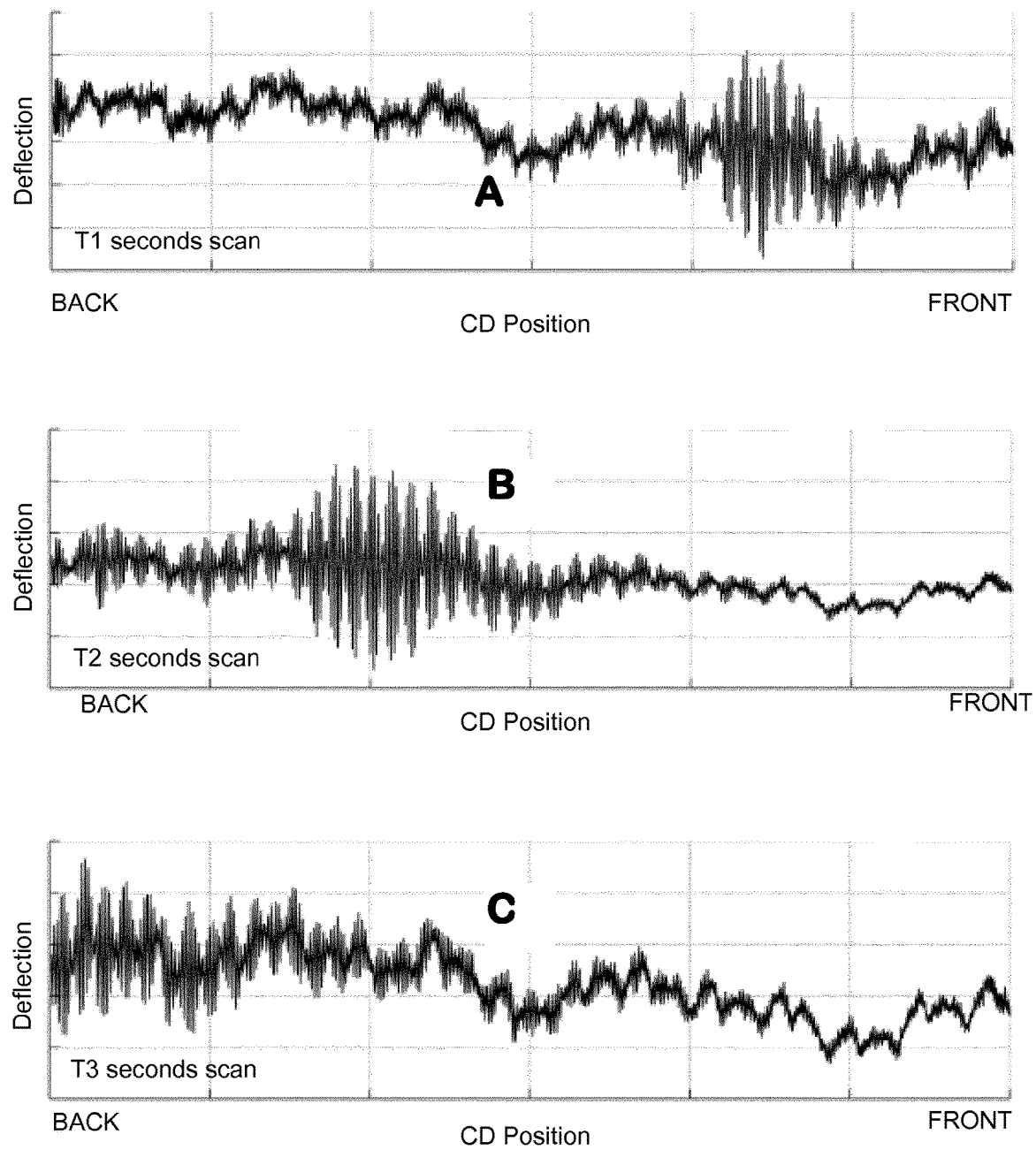
FIG. 17 shows graphs illustrating deflection profiles with high frequency oscillations being performed when the blocking device is arranged so as to block a sub-area of the radiation in cross direction CD according to embodiments.

FIG. 17 shows graphs illustrating deflection profiles with high frequency oscillations observed when the blocking device is arranged so as to block a sub-area of the radiation R in cross direction CD. As the scanning apparatus 100 traverses back and forth, the partially-blocked scanning measurement 401 obtained from the partially blocked scanning signal 141 obtained from different scans performed at different scan speeds A, B and C may exhibit high frequency oscillations at different CD positions. Accordingly, the extracted deflection characteristics can include high frequency oscillations at different CD positions for different scan speeds A, B and C. Such deflection variations may be associated with natural vibrations of the scanning mechanism. Changing the carriage payload or belt stiffness or applying proper lubrication may reduce this type of deflection oscillations in practice. FIG. 17 show an example of vibrations that appear at difference CD positions at different scan speeds A, B and C.

Figure 18:
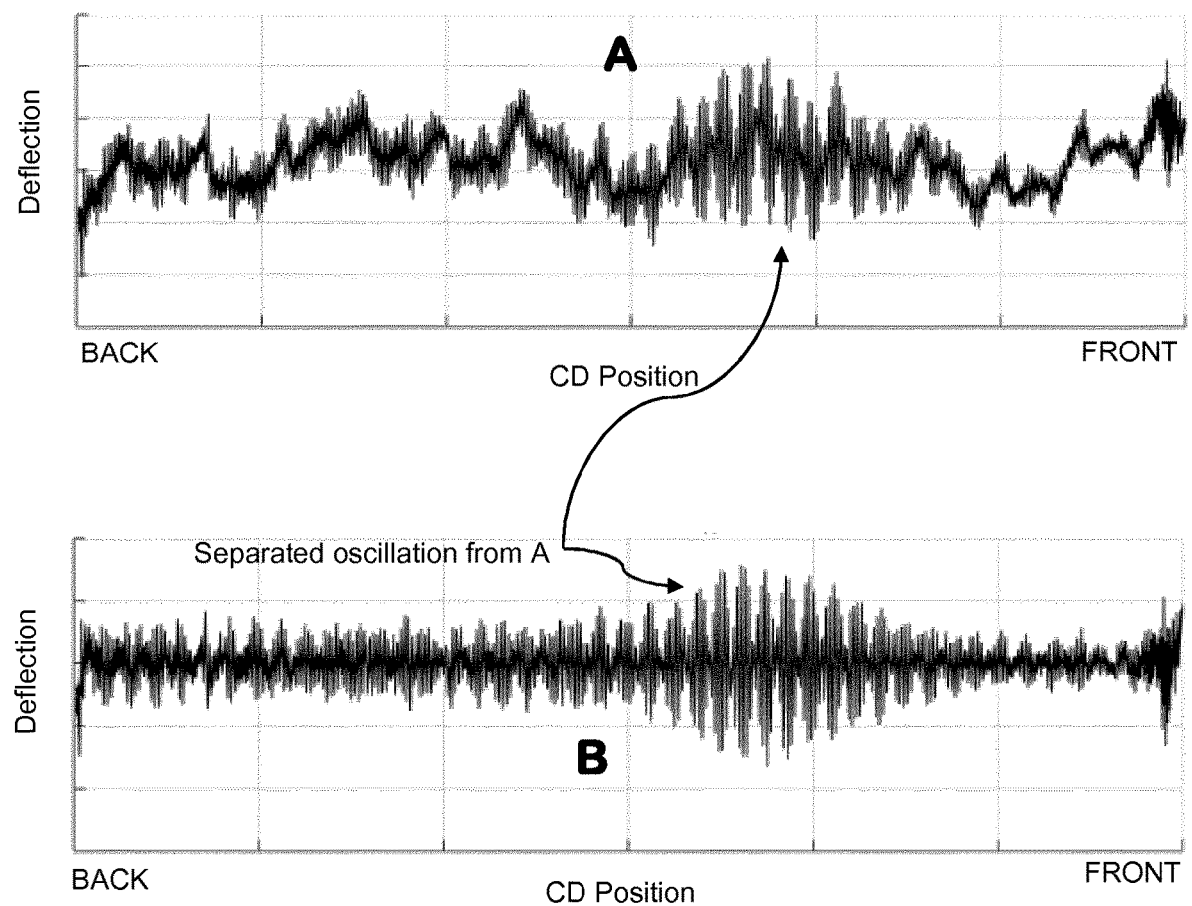
FIG. 18 shows a graph illustrating a CD deflection profile, with beating amplitude according to embodiments.

FIG. 18 shows a graph illustrating a CD deflection profile, with beating amplitude. The partially-blocked scanning measurement 401 obtained from the partially blocked sensor signal 141 may contain high frequency vibrations (as shown in the previous case) and with beat amplitude. The extracted deflection characteristics can thus include a beating amplitude in addition to the high frequency oscillations at different CD positions for different scan speeds A and B. The beating amplitude can be an indication that both the lower carriage 330 and the upper carriage 340 are vibrating simultaneously but they have slightly different natural frequencies. Accordingly, the associated condition can be vibrations in the scanning apparatus mechanics 300. FIG. 18 indicates that there can be at least two slightly different frequencies associated with the vibrations.

Figure 19:
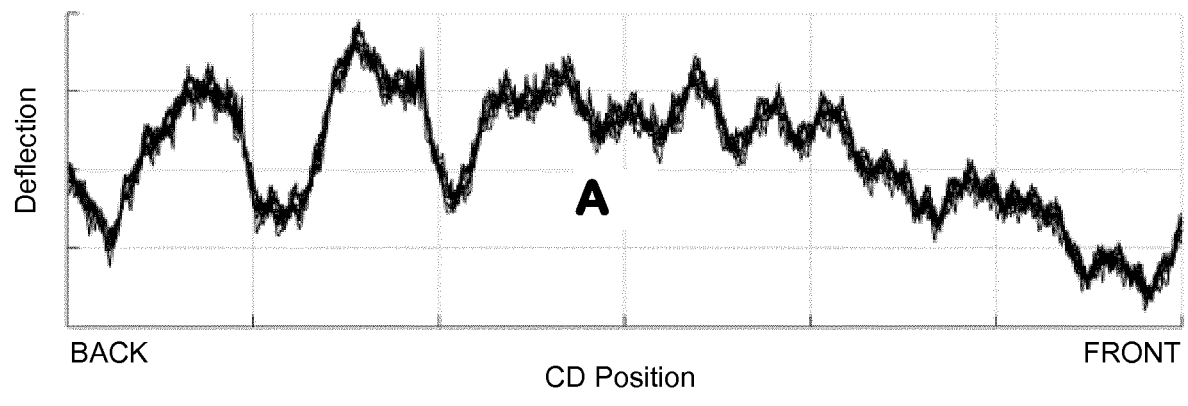
FIG. 19 shows graphs illustrating a deflection profile with oscillations with multiple harmonics and its corresponding power spectrum according to embodiments.
Figure 19:
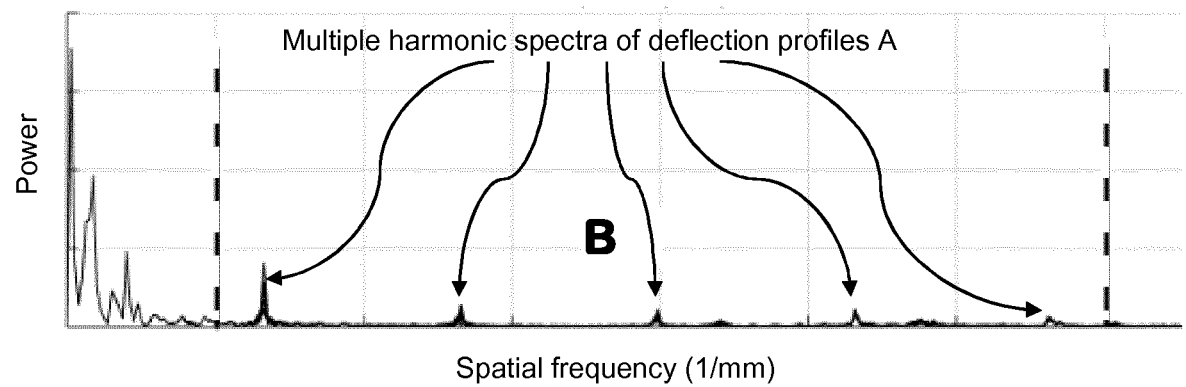

FIG. 19 shows graphs illustrating a deflection profile with oscillations with multiple harmonics and its corresponding power spectrum. As shown in the power spectrum, the multiple harmonics can be of the same primary frequency of an oscillating deflection. Accordingly, the extracted deflection characteristics can be an oscillation with multiple harmonics. Specifically, the partially-blocked scanning measurement 401 obtained from the partially blocked sensor signal 141 may contain variations with multiple distinguishable harmonic frequencies of the same primary frequency that matches with rotating mechanical components. Combining the primary and its harmonic variations can be a good indication of the damaged or defected rotating parts such as carriage wheels, drive gears, etc. Accordingly, the associated condition can be damaged or defected rotating parts such as carriage wheels, drive gears, etc. FIG. 19 shows an examples of damaged carriage wheels.

Figure 20:
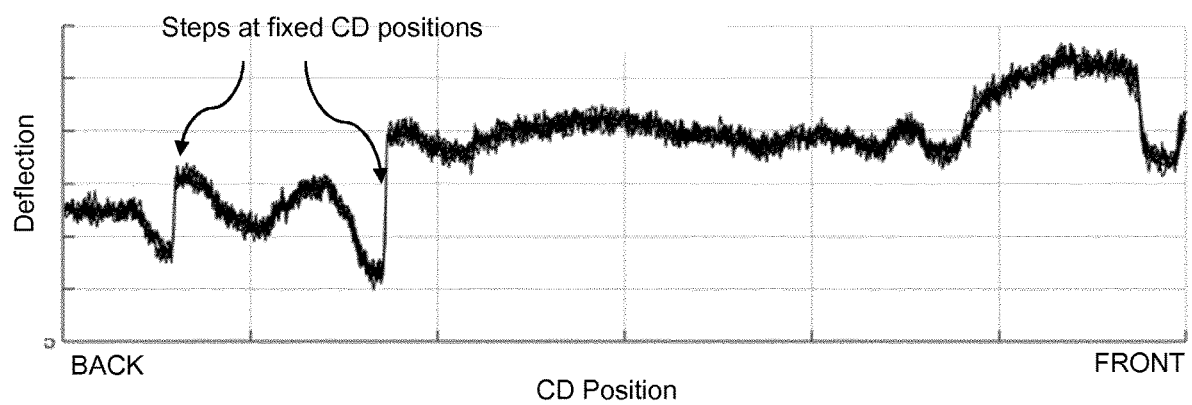
FIG. 20 shows a graph illustrating a MD deflection profile including steps or spikes at fixed CD positions according to embodiments.

FIG. 20 shows a graph illustrating a MD deflection profile including steps or spikes at fixed CD position. The deflection profile can be obtained when the blocking device 200 is arranged so as to partially block the detection module aperture 142 in the machine direction MD. As the scanning apparatus 100 traverses back and forth, the partially-blocked scanning measurement 401 obtained from the partially blocked scanning signal 141 may exhibit a pair of steps or spikes at several fixed CD positions. Accordingly, the extracted deflection characteristics can include a pair of steps or spikes at several fixed CD positions. These pair of steps or spikes may indicate unexpected damage or non-smooth spots on the guiderails 360. Accordingly, the associated condition can be damage or non-smooth spots on the guiderails 360. Specifically, deflection steps or spikes can appear as the carriage wheels 350 moves pass these non-smooth spots. The distance between the steps or spikes of each pair matches with the wheel distance on the carriages. The pair of deflection steps or spikes can be indicators of guiderail non-smoothness, defects or damages.

Figure 21:
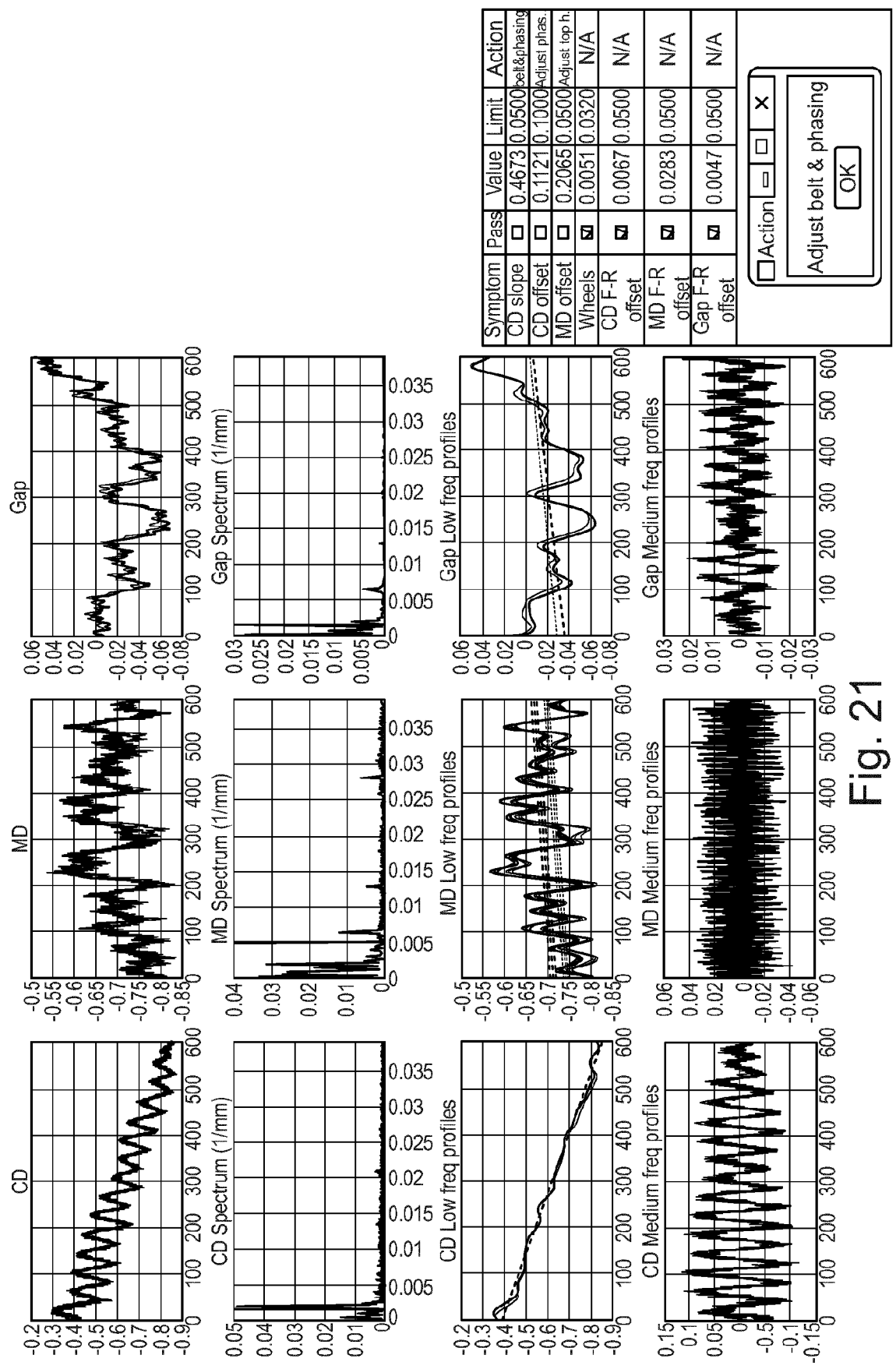
FIG. 21 shows a layout a tool according to embodiments.

While deflection characteristics can be separated and analyzed by experts who are familiar with scanning apparatus mechanics 300, a typical service engineer or technician may not have the skill or tools to extract these deflection characteristics for troubleshooting the mechanical issues of the scanning apparatus 100. To assist a service engineer or technician to qualify and/or quantify machine conditions, conduct diagnostics of scanner apparatus, and performance scanner maintenance, an analysis tool based on the method described herein is provided. FIG. 21 shows a layout of such a tool. The tool or analysis tool can perform importing of scanning measurement, converting to deflection profiles, plotting deflection profiles, applying spectral analysis of deflection profiles, extracting deflection characteristics, associating extracted deflection characteristics with various mechanical conditions and operation of the scanning apparatus and eventually recommending courses of actions needed to correct or reduce mechanical conditions that exceed the acceptable limits. FIG. 22 shows an example of Root Cause Analysis (RCA) table and recommended actions. By clicking the Action follows the mechanical conditions that exceed the limit, service engineers or technicians get recommended actions for resolving the corresponding issues.

In practice, the present disclosure allows engineers or service personnel to obtain deflection measurements of a scanning apparatuses 100 without acquiring additional sensor, alternation of the existing scanner, and/or upgrade QCS software. The deflection measurements obtained with the present disclosure provides detailed insights into the mechanical conditions of a scanning apparatus 100. The present disclosure can be applied while a sheet-making process is running or in shutdown maintenance conditions. Beneficial values to sheet makers are: i) The present disclosure can be easily applied to the majority of existing scanning apparatuses without any additional cost or modification. It can be applied in as short as 30 minutes up to one or two hours to get complete set of deflection information about a scanning apparatus 100 mechanical conditions. Also, there is no special skill needed to apply the present invention other than basic QCS scanning apparatus 100 maintenance knowledge; ii) Detailed information about the mechanical conditions of a QCS scanning apparatus 100 is relevant to ensure the accuracy of sheet quality measurements. If the deflections of a QCS scanning apparatus 100 exceed acceptable limits and not being detected accurately, sheet-making machine may produce tons of out of spec products without being noticed and those sheet products may be rejected from their downstream customers or consumers. The result could be very costly for sheet-makers; and iii) Having detailed deflection information of a QCS scanning apparatus 100, service and/or maintenance personnel can determine which mechanical parts need services, fine-tuning, or replacement. With the present disclosure being applied periodically and the measured deflections being recorded accordingly, service personnel can schedule needed maintenance on a timely basis and keep QCS scanning apparatus 100 always operate at good conditions. As the result, sheet-makers can have a reliable QCS scanning apparatus 100 to support their production.

While the foregoing is directed to embodiments of the disclosure, other and further embodiments of the disclosure may be devised without departing from the basic scope thereof, and the scope thereof is determined by the claims that follow.

The invention claimed is:

1. A method for detecting a deflection between a source module and a detection module in a scanning apparatus and configured as a sensor pair for scanning transmission measurement of sheet material transported in a machine direction through a sensing gap formed between the source module and the detection module,
   the source module arranged on a first side of the sensing gap and emitting a sensing radiation towards the sensing gap, and
   the detection module arranged on a second side of the sensing gap opposite to the first side and detecting the radiation from the source module and transmitted through the sensing gap, the method comprising:
   attaching a removable blocking device to the detection module, so that a radiation-blocking area of the blocking device partially blocks, in an asymmetrical manner, a sub-area of the cross-sectional area of the radiation impinging onto a detection module aperture of the detection module; and
   performing a partially-blocked scanning process during which the source module and the detection module are jointly moved in a cross direction of the scanning apparatus, the source module emits the radiation and the detection module detects the radiation from the source module having transmitted through the sensing gap,
   whereby a selected portion of the radiation corresponding to the sub-area covered by the radiation-blocking area is blocked from detected by the detection module aperture,
   whereby a partially-blocked sensor signal is obtained from the radiation detected by the detection module.

2. The method according to claim 1, wherein the deflection is used as a diagnostics of conditions of mechanical components or operations of the scanning apparatus, specifically for quantification of mechanical conditions, diagnostics or maintenance of scanning apparatus, particularly wherein, the conditions of mechanical components or operations of the scanning apparatus include any or all of the following attributes of a scanning apparatus mechanics:
   a) tension differential between lower drive belt and upper drive belt;
   b) phasing adjustment of lower drive pulley versus upper drive pulley;
   c) eccentricity of lower drive pulley or upper drive pulley;
   d) eccentricity of lower idler pulley or upper idler pulley;
   e) backlash between lower drive pulley and upper drive pulley;
   f) roundness of wheels on lower carriage and/or upper carriage;
   g) contact uniformity of wheels on guiderails;
   h) straightness, defects and debris on guiderails;
   i) fastening and alignment of source module and detection module onto their corresponding lower carriage and upper carriage;
   j) vibrations in the scanning apparatus mechanics caused by external excitation from other process machinery in the vicinity of the scanning apparatus; and
   k) vibrations in the scanning apparatus mechanics caused by internal excitation from any of the subsystems of the scanning apparatus mechanics.

3. The method according to claim 2, further comprising:
   calculating the deflection between the source module and the detection module from the sensor signal obtained from the detection module is processed by a system for providing a partially-blocked scanning measurement as a function of cross direction position, particularly wherein the calculating step provides a conversion from partially-blocked scanning measurement to a deflection profile in a unit of length.

4. The method according to claim 2, wherein the asymmetric partially blocking area of the blocking device is arranged to make the measurement signal primarily sensitive to deflections in the machine direction, particularly wherein the blocking area of the blocking device is configured to block opposing halves of detection module aperture in a downstream machine direction and a upstream machine direction, and wherein an averaged deflection in machine direction is calculated from the difference between the mean values of the deflection profile of the detection module aperture blocked in the downstream machine direction and the upstream machine direction.

5. The method according to claim 2, wherein the asymmetric partially blocking area of the blocking device is arranged to make the measurement signal primarily sensitive to deflections in the cross direction, particularly wherein the blocking area of the blocking device is configured to block opposing halves of the detection module aperture in a back cross direction and a front cross direction, and wherein an averaged deflection in cross direction is calculated from a difference between the mean values of the deflection profile of the detection module aperture blocked in the back cross direction and the front cross direction.

6. The method according to claim 2, wherein multiple passes of the partially-blocked scanning process are performed, wherein the radiation-blocking area of the blocking device is turned by a predetermined angle after a number of scans of the partially-blocked scanning process in order to separately evaluate deflections in both machine direction and cross direction.

7. The method according to claim 1, further comprising:
calculating the deflection between the source module and the detection module from the sensor signal obtained from the detection module is processed by a system for providing a partially-blocked scanning measurement as a function of cross direction position, particularly wherein the calculating step provides a conversion from partially-blocked scanning measurement to a deflection profile in a unit of length.

8. The method according to claim 7, wherein using the deflection as diagnostics of conditions of mechanical components or operations of the scanning apparatus, specifically for quantification of mechanical conditions, diagnostics or maintenance of scanning apparatus, includes extracting deflection characteristics from the deflection profile and associating the extracted deflection characteristics with the conditions of mechanical components or operations of the scanning apparatus specifically for quantification of mechanical conditions, diagnostics or maintenance of scanning apparatus.

9. The method according to claim 8, wherein, in the extracting and associating step, power spectra are obtained from the deflection profile for forward and reverse scan directions, particularly wherein the deflection characteristics includes a deflection difference between the forward and reverse scan directions and/or wherein the measurement characteristics includes a high frequency oscillation occurring at certain sections of the cross direction during the forward and reverse scan directions.

10. The method according to claim 9, wherein the deflection characteristics includes a pair of steps or spikes at fixed positions in cross direction, a slope in the cross direction of the deflection profile, an oscillation of the deflection profile, a high frequency oscillation with beating amplitude of the deflection profile, a high frequency oscillation multiple harmonics associated to the same primary frequency of the deflection profile, and/or an uneven variation of the deflection profile.

11. The method according to claim 8, wherein the deflection characteristics includes a pair of steps or spikes at fixed positions in cross direction, a slope in the cross direction of the deflection profile, an oscillation of the deflection profile, a high frequency oscillation with beating amplitude of the deflection profile, a high frequency oscillation multiple harmonics associated to the same primary frequency of the deflection profile, and/or an uneven variation of the deflection profile.

12. The method according to claim 1, wherein the asymmetric partially blocking area of the blocking device is arranged to make the measurement signal primarily sensitive to deflections in the machine direction, particularly wherein the blocking area of the blocking device is configured to block opposing halves of detection module aperture in a downstream machine direction and a upstream machine direction, and wherein an averaged deflection in machine direction is calculated from the difference between the mean values of the deflection profile of the detection module aperture blocked in the downstream machine direction and the upstream machine direction.

13. The method according to claim 1, wherein the asymmetric partially blocking area of the blocking device is arranged to make the measurement signal primarily sensitive to deflections in the cross direction, particularly wherein the blocking area of the blocking device is configured to block opposing halves of the detection module aperture in a back cross direction and a front cross direction, and wherein an averaged deflection in cross direction is calculated from a difference between the mean values of the deflection profile of the detection module aperture blocked in the back cross direction and the front cross direction.

14. The method according to claim 1, wherein multiple passes of the partially-blocked scanning process are performed, wherein the radiation-blocking area of the blocking device is turned by a predetermined angle after a number of scans of the partially-blocked scanning process in order to separately evaluate deflections in both machine direction and cross direction.

15. The method according to claim 1, wherein the scanning process is performed with moving sheet material in the sensing gap between the source module and the detection module or wherein the scanning process is performed in absence of any moving sheet material in the sensing gap between the source module and the detection module.

16. A scanning apparatus configured for scanning transmission measurement of sheet material transported in a machine direction through a sensing gap of the scanning apparatus, comprising:
a source module arranged on a first side of the sensing gap and configured to emit a sensing radiation towards the sensing gap;
a detection module arranged on a second side of the sensing gap opposite to the first side and configured to detect the radiation from the source module and transmitted through the sensing gap; and
a blocking device temporarily fixed to the detection module, so that a radiation-blocking area of the blocking device in an asymmetrical manner partially blocks a sub-area of the transverse cross-sectional area of the radiation impinging onto a detection module aperture of the detection module,
wherein the source module and the detection module are configured to be jointly moved in the cross direction of the scanning apparatus to detect a deflection of the source module and the detection module.

17. The scanning apparatus according to claim 16, wherein the radiation-blocking area of the blocking device has a straight edge in the transverse cross-sectional area of the radiation, so that the sub-area covered by the radiation-blocking area extends from the edge of detector window to the straight edge, whereas the other side of the straight edge is unobstructed by the radiation-blocking material, particularly wherein the straight edge of the radiation-blocking area is arranged according to at least one of a to c:
  a) the straight edge extends through the entire cross-sectional area of the radiation,
  b) the straight edge includes the centrum of the cross-sectional area of the radiation,
  c) the straight edge extends along the machine direction or the cross direction.

18. The scanning apparatus according to claim 16, wherein the blocking device is configured to block half of the radiation reaching the detection module aperture.

19. The scanning apparatus according to claim 16, wherein the blocking area of the blocking device is configured to block an opposing half of detection module aperture in upstream machine direction, downstream machine direction, back cross direction and front cross direction.

20. A blocking device for detecting a deflection in a scanning apparatus configured for scanning transmission measurement of sheet material transported in a machine direction through a sensing gap formed between a source module and a detection module of the scanning apparatus from a partially-blocked sensor signal obtained from a partially-blocked scanning process,
  the source module arranged on a first side of the sensing gap and emitting a scanning radiation towards the sensing gap, and the detection module arranged on a second side of the sensing gap opposite to the first side and detecting the radiation from the source module and transmitted through the sensing gap,
  during the partially-blocked scanning process the source module and the detection module jointly moved in a cross direction of the scanning apparatus, the source module emitting the radiation and the detection module detecting the radiation from the source module having transmitted through the sensing gap, whereby a selected portion of the radiation corresponding to the sub-area covered by the radiation-blocking area is blocked from reaching the detection module, whereby the partially-blocked sensor signal is obtained from the radiation detected by the detection module.

* * * * *